(12) United States Patent
Lee et al.

(10) Patent No.: US 11,471,056 B2
(45) Date of Patent: *Oct. 18, 2022

(54) MEDICAL IMAGING DEVICE AND METHODS OF USE

(71) Applicant: Lumicell, Inc., Wellesley, MA (US)

(72) Inventors: W. David Lee, Brookline, MA (US); Jorge Ferrer, Arlington, MA (US); David B. Strasfeld, Cambridge, MA (US)

(73) Assignee: Lumicell, Inc., Newton, MA (US)

( * ) Notice: Subject to any disclaimer, the term of this patent is extended or adjusted under 35 U.S.C. 154(b) by 1360 days.

This patent is subject to a terminal disclaimer.

(21) Appl. No.: 15/206,754

(22) Filed: Jul. 11, 2016

(65) Prior Publication Data

US 2016/0317037 A1 Nov. 3, 2016

Related U.S. Application Data

(63) Continuation of application No. 14/211,201, filed on Mar. 14, 2014, now Pat. No. 10,791,937.

(Continued)

(51) Int. Cl.
*A61B 5/00* (2006.01)
*A61B 90/00* (2016.01)
(Continued)

(52) U.S. Cl.
CPC .......... *A61B 5/0091* (2013.01); *A61B 5/0071* (2013.01); *A61B 5/0075* (2013.01); *A61B 5/0086* (2013.01); *A61B 5/4312* (2013.01); *A61B 10/0041* (2013.01); *A61B 90/361* (2016.02); *A61K 49/0032* (2013.01); *A61K 49/0056* (2013.01); *A61B 5/6886* (2013.01); *A61B 2090/306* (2016.02); *A61B 2090/309* (2016.02); *A61B 2090/3616* (2016.02);
(Continued)

(58) Field of Classification Search
None
See application file for complete search history.

(56) References Cited

U.S. PATENT DOCUMENTS 4,947,245 A * 8/1990 Ogawa ............... A61B 1/00101
348/66
5,268,486 A 12/1993 Waggoner et al.
(Continued)

FOREIGN PATENT DOCUMENTS

EP 1065250 A1 1/2001
EP 1211294 A1 6/2002
(Continued)

OTHER PUBLICATIONS

Dacosta et al., New optical technologies for earlier endoscopic diagnosis of premalignant gastrointestinal lesions. J Gastroenterol Hepatol. Feb. 2002;17 Suppl:S85-104.
(Continued)

*Primary Examiner* — Katherine L Fernandez
*Assistant Examiner* — Michael S Kellogg
(74) *Attorney, Agent, or Firm* — Wolf, Greenfield & Sacks, P.C.

(57) ABSTRACT

Embodiments related to medical imaging devices including rigid imaging tips and their methods of use for identifying abnormal tissue within a surgical bed are disclosed.

28 Claims, 21 Drawing Sheets

Related U.S. Application Data

(60) Provisional application No. 61/785,136, filed on Mar. 14, 2013, provisional application No. 61/781,601, filed on Mar. 14, 2013.

(51) Int. Cl.
    *A61K 49/00*      (2006.01)
    *A61B 10/00*      (2006.01)
    *A61B 90/30*      (2016.01)

(52) U.S. Cl.
    CPC ... *A61B 2090/3941* (2016.02); *A61B 2505/05* (2013.01); *A61B 2560/0431* (2013.01)

(56) References Cited

U.S. PATENT DOCUMENTS

| | | | |
|---|---|---|---|
| 5,366,860 A | 11/1994 | Bergot et al. | |
| 5,438,989 A | 8/1995 | Hochman et al. | |
| 5,569,587 A | 10/1996 | Waggoner | |
| 5,593,658 A | 1/1997 | Bogdanov et al. | |
| 5,647,368 A | 7/1997 | Zeng et al. | |
| 5,688,221 A | 11/1997 | Yabe et al. | |
| 5,716,321 A * | 2/1998 | Kerin | A61B 1/0008 600/104 |
| 5,749,830 A | 5/1998 | Kaneko | |
| 5,769,791 A | 6/1998 | Benaron et al. | |
| 5,800,995 A | 9/1998 | Patonay et al. | |
| 5,825,502 A | 10/1998 | Mayer | |
| 5,954,634 A * | 9/1999 | Igarashi | A61B 1/055 600/109 |
| 5,968,479 A | 10/1999 | Ito et al. | |
| 6,027,709 A | 2/2000 | Little et al. | |
| 6,032,071 A | 2/2000 | Binder | |
| 6,069,689 A | 5/2000 | Zeng et al. | |
| 6,083,486 A | 7/2000 | Weissleder et al. | |
| 6,122,042 A | 9/2000 | Wunderman et al. | |
| 6,136,612 A | 10/2000 | Della Ciana et al. | |
| 6,180,086 B1 | 1/2001 | Achilefu et al. | |
| 6,256,530 B1 | 7/2001 | Wolfe | |
| 6,403,625 B1 | 6/2002 | Nagao et al. | |
| 6,485,413 B1 | 11/2002 | Boppart et al. | |
| 6,537,211 B1 | 3/2003 | Wang et al. | |
| 6,592,847 B1 | 7/2003 | Weissleder et al. | |
| 6,620,621 B1 | 9/2003 | Cohenford et al. | |
| 6,631,230 B1 | 10/2003 | Campbell | |
| 6,667,159 B1 | 12/2003 | Walt et al. | |
| 6,737,247 B2 | 5/2004 | Bogdanov et al. | |
| 6,834,238 B1 | 12/2004 | Hochman | |
| 6,837,867 B2 * | 1/2005 | Kortelling | A61M 25/0144 604/95.01 |
| 7,128,894 B1 | 10/2006 | Tannous et al. | |
| 7,285,089 B2 | 10/2007 | Viellerobe et al. | |
| 7,344,530 B2 | 3/2008 | Bischof et al. | |
| 7,383,076 B2 | 6/2008 | Ntziachristos et al. | |
| 7,383,077 B2 | 6/2008 | Zeng | |
| 7,452,727 B2 | 11/2008 | Hennig et al. | |
| 7,498,029 B2 | 3/2009 | Hasan et al. | |
| 8,815,214 B2 | 8/2014 | Rajopadhye et al. | |
| 8,936,629 B2 | 1/2015 | Boyden et al. | |
| 8,983,581 B2 | 3/2015 | Bawendi et al. | |
| 9,032,965 B2 | 5/2015 | Lee | |
| 9,155,471 B2 | 5/2015 | Lee | |
| 9,314,304 B2 | 4/2016 | Lee et al. | |
| 9,532,835 B2 | 1/2017 | Lee | |
| 2002/0064794 A1 | 5/2002 | Leung et al. | |
| 2002/0115862 A1 | 8/2002 | Czerney et al. | |
| 2002/0139920 A1 | 10/2002 | Seibel et al. | |
| 2002/0165456 A1 | 11/2002 | Canpolat et al. | |
| 2003/0029741 A1 | 2/2003 | Carver et al. | |
| 2003/0044353 A1 | 3/2003 | Weissleder et al. | |
| 2003/0138378 A1 | 7/2003 | Hashimshony | |
| 2004/0015062 A1 | 1/2004 | Ntziachristos et al. | |
| 2004/0071332 A1 | 4/2004 | Bruce et al. | |
| 2004/0147843 A1 | 7/2004 | Bambot et al. | |
| 2004/0186363 A1 | 9/2004 | Smit et al. | |
| 2004/0253593 A1 | 12/2004 | Cai et al. | |
| 2005/0130167 A1 | 6/2005 | Bao et al. | |
| 2005/0171434 A1 | 8/2005 | Madden et al. | |
| 2005/0207668 A1 | 9/2005 | Perchant et al. | |
| 2005/0214221 A1 | 9/2005 | Poss et al. | |
| 2006/0009590 A1 | 1/2006 | Kozlowski et al. | |
| 2006/0089554 A1 | 4/2006 | Ishihara et al. | |
| 2006/0165350 A1 | 7/2006 | Gelikonov et al. | |
| 2006/0188797 A1 | 8/2006 | Roy et al. | |
| 2006/0253107 A1 | 11/2006 | Hashimshony et al. | |
| 2007/0036725 A1 | 2/2007 | Bogyo et al. | |
| 2007/0049795 A1 | 3/2007 | Miyagi et al. | |
| 2007/0160279 A1 | 7/2007 | Demos | |
| 2007/0179174 A1 | 8/2007 | Bachurin et al. | |
| 2007/0182959 A1 | 8/2007 | Maier et al. | |
| 2007/0232874 A1 | 10/2007 | Ince | |
| 2007/0255169 A1 | 11/2007 | Hashimshony et al. | |
| 2007/0260156 A1 | 11/2007 | Hashimshony | |
| 2008/0015446 A1 | 1/2008 | Mahmood et al. | |
| 2008/0029711 A1 | 2/2008 | Viellerobe et al. | |
| 2008/0039742 A1 | 2/2008 | Hashimshony et al. | |
| 2008/0045799 A1 | 2/2008 | Whitehead et al. | |
| 2008/0058795 A1 | 3/2008 | Boyden et al. | |
| 2008/0076674 A1 | 3/2008 | Litman et al. | |
| 2008/0103373 A1 | 5/2008 | Matter et al. | |
| 2008/0116392 A1 | 5/2008 | Brooker | |
| 2008/0119832 A1 | 5/2008 | Cronin | |
| 2008/0154102 A1 | 6/2008 | Frangioni et al. | |
| 2008/0193373 A1 | 8/2008 | Stritzker et al. | |
| 2008/0193431 A1 | 8/2008 | Zheng et al. | |
| 2008/0241065 A1 | 10/2008 | Benaron et al. | |
| 2008/0260646 A1 | 10/2008 | Keller et al. | |
| 2008/0287750 A1 | 11/2008 | Hashimshony et al. | |
| 2009/0004116 A1 | 1/2009 | Bhaumik et al. | |
| 2009/0028788 A1 | 1/2009 | Achilefu | |
| 2009/0123381 A1 | 5/2009 | Hsieh et al. | |
| 2009/0202119 A1 | 8/2009 | Hefti et al. | |
| 2009/0220430 A1 | 9/2009 | Rajopadhye et al. | |
| 2009/0239755 A1 | 9/2009 | Thastrup et al. | |
| 2009/0299196 A1 * | 12/2009 | Bawendi | A61B 5/4848 600/478 |
| 2010/0049058 A1 | 2/2010 | Ishihara et al. | |
| 2010/0168586 A1 | 7/2010 | Hillman et al. | |
| 2010/0189658 A1 | 7/2010 | Wendt et al. | |
| 2010/0262017 A1 | 10/2010 | Frangioni et al. | |
| 2010/0286044 A1 | 11/2010 | Litman et al. | |
| 2010/0298554 A1 | 11/2010 | Laikhter et al. | |
| 2010/0321772 A1 | 12/2010 | Reimer et al. | |
| 2011/0009694 A1 * | 1/2011 | Schultz | A61B 1/00105 600/109 |
| 2011/0021908 A1 | 1/2011 | Lee et al. | |
| 2011/0028790 A1 | 2/2011 | Farr et al. | |
| 2011/0042580 A1 | 2/2011 | Wilson et al. | |
| 2011/0104071 A1 | 5/2011 | Lee et al. | |
| 2011/0159566 A1 | 6/2011 | Josephson et al. | |
| 2011/0201884 A1 | 8/2011 | Kishioka | |
| 2012/0150164 A1 | 6/2012 | Lee et al. | |
| 2014/0088384 A1 | 3/2014 | Basillion | |
| 2014/0207126 A1 | 7/2014 | Bianchi | |
| 2014/0207129 A1 | 7/2014 | Lee | |
| 2014/0243934 A1 | 8/2014 | Vo-Dinh et al. | |
| 2014/0276102 A1 | 9/2014 | Lee et al. | |
| 2014/0276103 A1 | 9/2014 | Lee et al. | |
| 2014/0301950 A1 | 10/2014 | Lee et al. | |
| 2015/0216416 A1 | 8/2015 | Bawendi et al. | |
| 2015/0216600 A1 | 8/2015 | Lee et al. | |
| 2016/0025632 A1 | 1/2016 | Lee et al. | |

FOREIGN PATENT DOCUMENTS

| | | |
|---|---|---|
| EP | 1223197 A2 | 7/2002 |
| EP | 1273584 A1 | 1/2003 |
| JP | H09-024053 A | 1/1997 |
| JP | H10-309281 A | 11/1998 |
| JP | 2005-192944 A | 7/2005 |
| JP | 2005-195379 A | 7/2005 |
| JP | 2006-191989 A | 7/2006 |
| JP | 2007-511243 A | 5/2007 |

(56) References Cited

FOREIGN PATENT DOCUMENTS

| | | |
|---|---|---|
| JP | 2008-261784 A | 10/2008 |
| JP | 2010-259810 A | 11/2010 |
| JP | 2011-177419 A | 9/2011 |
| JP | 2011-255006 A | 12/2011 |
| JP | 2012-135475 A | 7/2012 |
| WO | WO 97/13810 A1 | 4/1997 |
| WO | WO 98/47538 A2 | 10/1998 |
| WO | WO 00/53678 A1 | 9/2000 |
| WO | WO 01/90253 A1 | 11/2001 |
| WO | WO 01/95795 A2 | 12/2001 |
| WO | WO 02/24815 A1 | 3/2002 |
| WO | WO 02/056670 A2 | 7/2002 |
| WO | WO 02/56670 A2 | 7/2002 |
| WO | WO 03/105814 A1 | 12/2003 |
| WO | WO 2004/058058 A1 | 7/2004 |
| WO | WO 2005/107579 A1 | 11/2005 |
| WO | WO 2008/078742 A1 | 3/2008 |
| WO | WO 2008/088865 A2 | 7/2008 |
| WO | WO 2010/138738 A1 | 12/2010 |

OTHER PUBLICATIONS

International Search Report and Written Opinion for PCT/US2014/027769 dated Oct. 30, 2014.
[No Author Listed], Cathepsin Activatable Fluorescent Probe. Clinical Trials. Jun. 21, 2012. (https://clinicaltrials.gov/archive/NCT01626066/2012_06_21) [last accessed May 27, 2015].
Anikijenko et al., In vivo detection of small subsurface melanomas in athymic mice using noninvasive fiber optic confocal imaging. J Invest Dermatol. Dec. 2001;117(6):1442-8.
Bach et al., Elevated lysosomal pH in Mucolipidosis type IV cells. Clin Chim Acta. Feb. 1999;280(1-2):173-9.
Bates et al., Short-range spectroscopic ruler based on a single-molecule optical switch. Phys Rev Lett. Mar. 18, 2005;94(10):108101. Epub Mar. 15, 2005.
Bigio et al., Diagnosis of breast cancer using elastic-scattering spectroscopy: preliminary clinical results. J Biomed Opt. Apr. 2000;5(2):221-8.
Blum et al., Noninvasive optical imaging of cysteine protease activity using fluorescently quenched activity-based probes. Nat Chem Biol. Oct. 2007;3(10):668-77. Epub Sep. 9, 2007.
Bogdanov, Jr. et al., Long-circulating blood pool imaging agents. Adv Drug Del Rev. 1995;16:335-48.
Brigman, Preliminary Analysis of Phase 1, First-In-Human, Cathepsin Activated Tumor Imaging Probe. Presentation. Nov. 2013. 29 pages.
Cheng et al., Near-infrared fluorescent RGD peptides for optical imaging of integrin alphavbeta3 expression in living mice. Bioconjug Chem. Nov.-Dec. 2005;16(6):1433-41.
Cuneo et al., Imaging primary mouse sarcomas after radiation therapy using cathepsin-activatable fluorescent imaging agents. Int J Radiat Oncol Biol Phys. May 1, 2013;86(1):136-42. doi: 10.1016/j.ijrobp.2012.12.007. Epub Feb. 4, 2013.
De Grand et al., Tissue-like phantoms for near-infrared fluorescence imaging system assessment and the training of surgeons. J Biomed Opt. Jan.-Feb. 2011;11(1):014007.
Demos et al., Near-infrared autofluorescence imaging for detection of cancer. J Biomed Opt. May-Jun. 2004;9(3):587-92.
Freireich et al., Quantitative comparison of toxicity of anticancer agents in mouse, rat, hamster, dog, monkey, and man. Cancer Chemother Rep. May 1966;50(4):219-44.
Funovics et al., Protease sensors for bioimaging. Anal Bioanal Chem. Nov. 2003;377(6):956-63. Epub Sep. 3, 2003.
Geigy Pharmaceuticals, Body Surface Area of Adults. In: Scientific Tables. Diem and Lentner, Ed., Ciba-Geigy Ltd. Ardsley, New York. 1970:537.
Goldberg et al., Radiofrequency tissue ablation: importance of local temperature along the electrode tip exposure in determining lesion shape and size. Acad Radiol. Mar. 1996;3(3):212-8.
Graves et al., A submillimeter resolution fluorescence molecular imaging system for small animal imaging. Med Phys. May 2003;30(5):901-11.
Gray et al., Dual-mode laparoscopic fluorescence image-guided surgery using a single camera. Biomed Opt Express. Aug. 1, 2012;3(8):1880-90. doi: 10.1364/BOE.3.001880. Epub Jul. 17, 2012.
Hart et al., Cell binding and internalization by filamentous phage displaying a cyclic Arg-Gly-Asp-containing peptide. J Biol Chem. Apr. 29, 1994;269(17):12468-74.
Holland et al., Chapter 4. Biodegradable polymers. In: Advances in Pharmaceutical Sciences. Ganderton et al., eds. vol. 6. 1992:101-164.
Holsinger et al., Use of the photonic band gap fiber assembly CO2 laser system in head and neck surgical oncology. Laryngoscope. Jul. 2006;116(7):1288-90.
Hsiung et al., Detection of colonic dysplasia in vivo using a targeted heptapeptide and confocal microendoscopy. Nat Med. Apr. 2008;14(4):454-8. doi: 10.1038/nm1692. Epub Mar. 16, 2008.
Kong et al., Comparative analysis of different laser systems to study cellular responses to DNA damage in mammalian cells. Nucleic Acids Res. May 2009;37(9):e68. doi: 10.1093/nar/gkp221. Epub Apr. 7, 2009.
Licha et al., Synthesis and characterization of cyanine dyes as contrast agents for near-infrared imaging. SPIE. 1996;2927:192-8.
Lin et al., Novel near-infrared cyanine fluorochromes: synthesis, properties, and bioconjugation. Bioconjug Chem. May-Jun. 2002;13(3):605-10.
Liu et al., Hands-free, wireless goggles for near-infrared fluorescence and real-time image-guided surgery. Surgery. May 2011;149(5):689-98. doi: 10.1016/j.surg.2011.02.007.
Mahmood et al., Near-infrared optical imaging of protease activity for tumor detection. Radiology. Dec. 1999;213(3):866-70.
Moats et al., A "Smart" Magnetic Resonance Imaging Agent That Reports on Specific Enzymatic Activity. Angew Chem Int Ed Engl. 1997;36(7):726-8.
Mullenix et al., Secondary operations are frequently required to complete the surgical phase of therapy in the era of breast conservation and sentinel lymph node biopsy. Am J Surg. May 2004;187(5):643-6.
Negrin et al., In vivo-in vitro study of biodegradable methadone delivery systems. Biomaterials. Mar. 2001;22(6):563-70.
Palen et al., Substrate specificity of a hypothalamic neurosecretory granule enzyme capable of processing pro-gonadotropin releasing hormone precursor protein. Peptides. Jan.-Feb. 1987;8(1):21-4. Abstract only.
Poul et al., Selection of tumor-specific internalizing human antibodies from phage libraries. J Mol Biol. Sep. 1, 2000;301(5):1149-61.
Railton et al., Myocardial scintigraphy with I-123 heptadecanoic acid as a test for coronary heart disease. Eur J Nucl Med. 1987;13(2):63-6.
Ramanujam et al., Fast and noninvasive fluorescence imaging of biological tissues in vivo using a flying-spot scanner. IEEE Trans Biomed Eng. Sep. 2001;48(9):1034-41.
Reinisch, Laser physics and tissue interactions. Otolaryngol Clin North Am. Dec. 1996;29(6):893-914.
Rogakou et al., Megabase chromatin domains involved in DNA double-strand breaks in vivo. J Cell Biol. Sep. 6, 1999;146(5):905-16.
Singletary et al., Revision of the American Joint Committee on Cancer staging system for breast cancer. J Clin Oncol. Sep. 1, 2002;20(17):3628-36.
Tung et al., In vivo imaging of proteolytic enzyme activity using a novel molecular reporter. Cancer Res. Sep. 1, 2000;60(17):4953-8.
Tyagi et al., Multicolor molecular beacons for allele discrimination. Nat Biotechnol. Jan. 1998;16(1):49-53.
Vaidya et al., Intraoperative T staging in radical retropubic prostatectomy: is it reliable? Urology. May 2001;57(5):949-54.
Van Eenige et al., Clinical value of studies with radioiodinated heptadecanoic acid in patients with coronary artery disease. Eur Heart J. Mar. 1990;11(3):258-68.
Vogel et al., Mechanisms of pulsed laser ablation of biological tissues. Chem Rev. Feb. 2003;103(2):577-644.

(56) References Cited

OTHER PUBLICATIONS

Weissleder et al., In vivo imaging of tumors with protease-activated near-infrared fluorescent probes. Nat Biotechnol. Apr. 1999;17(4):375-8.
Weissleder et al., In vivo magnetic resonance imaging of transgene expression. Nat Med. Mar. 2000;6(3):351-4.
Yang et al., Presentation, 2010 IVIS Imaging System from Caliper LifeSciences, 104 slide presentation 52 pages.
Zaheer et al., In vivo near-infrared fluorescence imaging of osteoblastic activity. Nat Biotechnol. Dec. 2001;19(12):1148-54.
Zornig et al., Re-excision of soft tissue sarcoma after inadequate initial operation. Br J Surg. Feb. 1995;82(2):278-9.

* cited by examiner

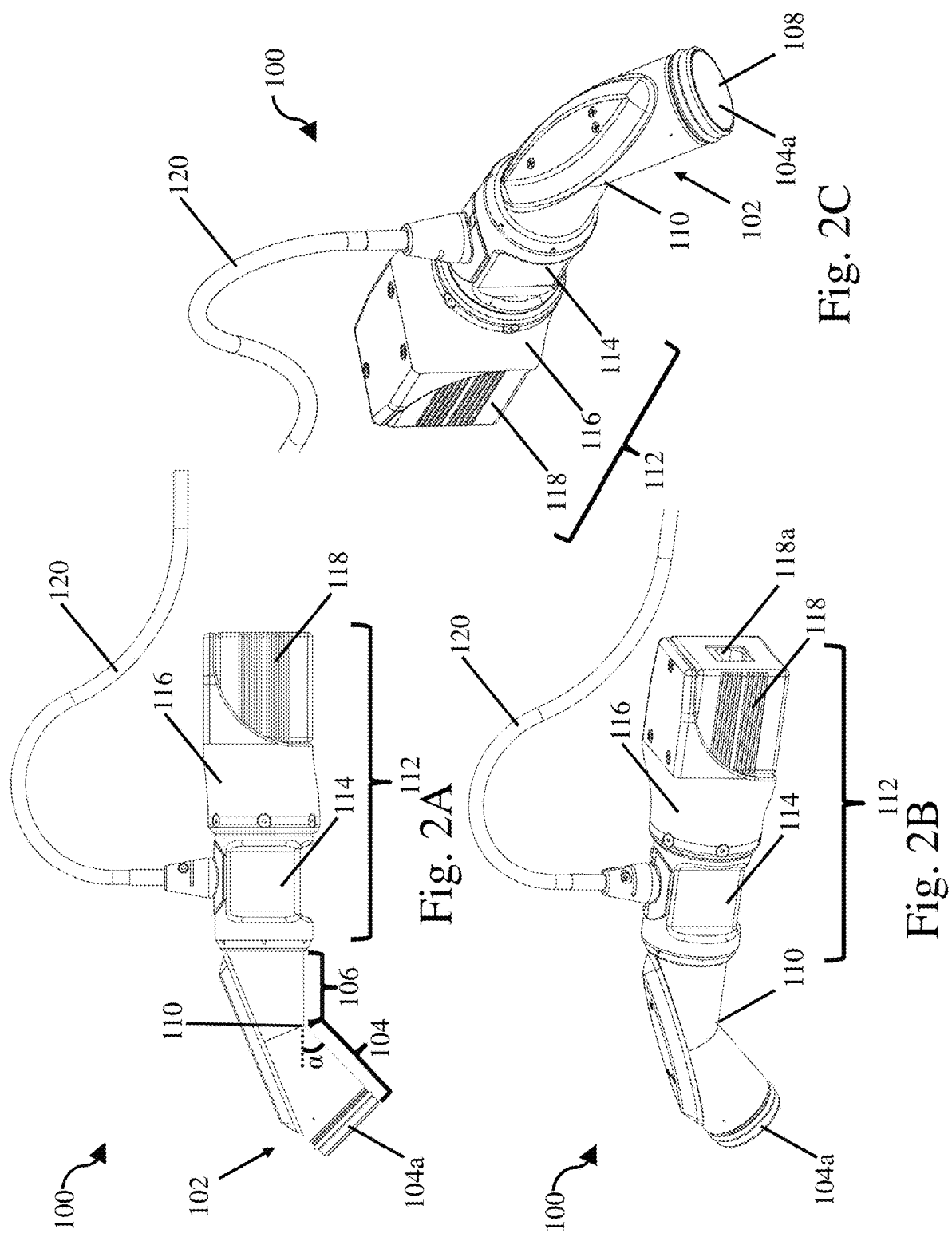

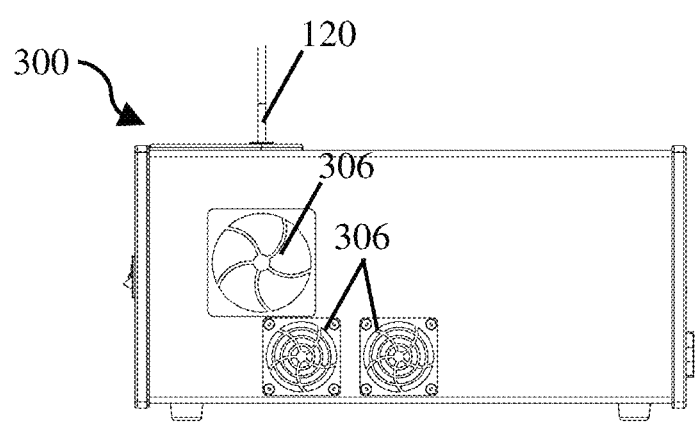
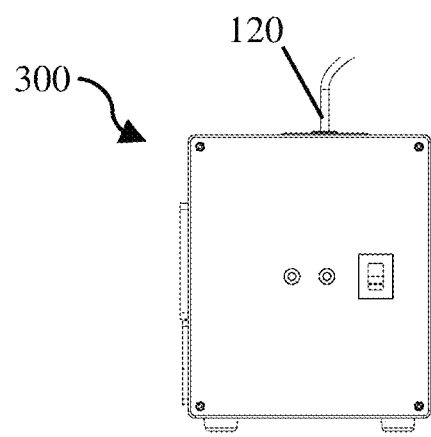
Fig. 8A
Fig. 8B
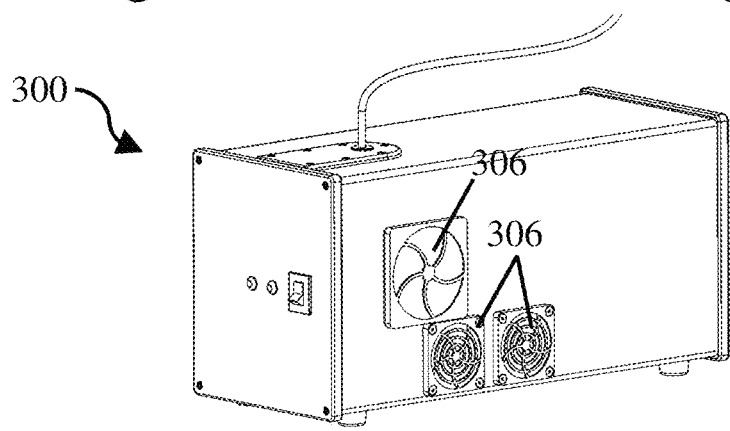
Fig. 8C
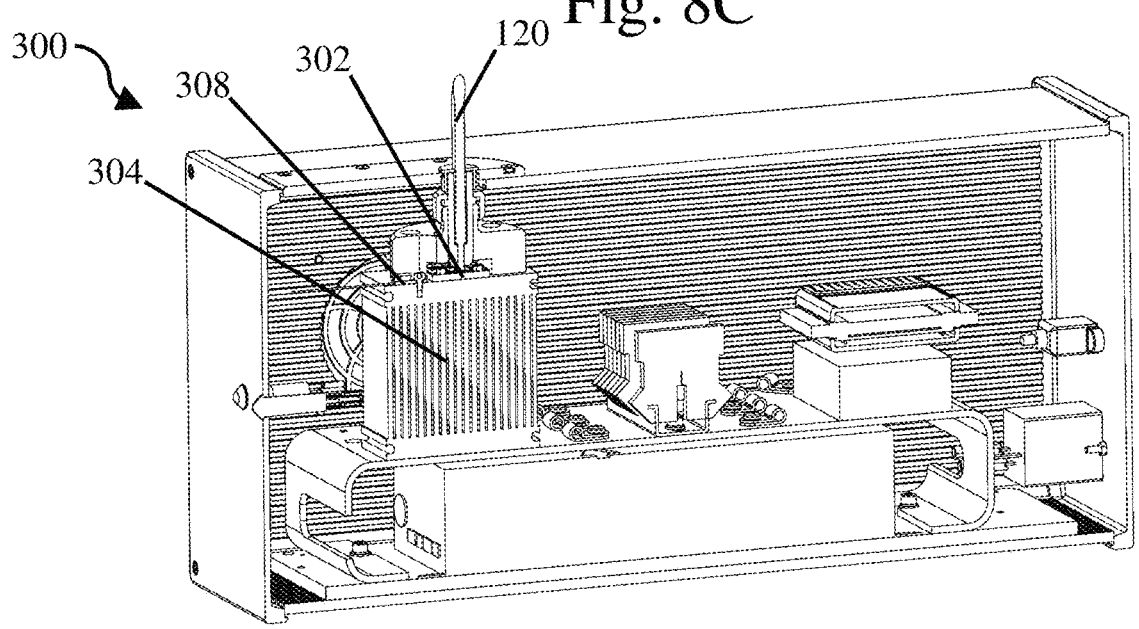
Fig. 8D

MEDICAL IMAGING DEVICE AND METHODS OF USE

CROSS-REFERENCE TO RELATED APPLICATIONS

This application is a continuation application claiming the benefit under 35 U.S.C. §120 of U.S. patent application Ser. No. 14/211,201, entitled "MEDICAL IMAGING DEVICE AND METHODS OF USE," filed on Mar. 14, 2014, which claims priority under 35 U.S.C. §119(e) to U.S. Provisional Application Ser. No. 61/781,601, entitled "IMAGING AGENT FOR DETECTION OF DISEASED CELLS" filed on Mar. 14, 2013 and U.S. Provisional Application Ser. No. 61/785,136, entitled "IMAGING AGENT FOR DETECTION OF DISEASED CELLS" filed on Mar. 14, 2013, each of which are herein incorporated by reference in their entirety.

GOVERNMENT LICENSE RIGHTS

This invention was made with government support under contract IIP-1152489 awarded by the National Science Foundation. The government has certain rights in the invention.

FIELD

Disclosed embodiments are related to medical imaging devices and their methods of use.

BACKGROUND

There are over one million cancer surgeries per year performed in the United States and nearly 40% of them miss resecting the entire tumor according to the National Cancer Institute Surveillance Epidemiology and End Results report. For example in breast cancer lumpectomies, failure to remove all of the cancer cells during the primary surgery (positive margins) occurs approximately 50% of the time and requires second surgeries. Residual cancer in the surgical bed is a leading risk factor for local tumor recurrence, reduced survival rates and increased likelihood of metastases. In addition, final histopathology of the resected tumor misses 25% of the residual cancer left in the surgical bed, which must be addressed with adjuvant medical therapy (e.g. radiotherapy or chemotherapy). This poor performance of pathology is primarily due to a sampling error since only a small fraction of the entire resection is analyzed.

In a typical solid tumor resection, the surgeon removes the bulk of the tumor and sends it to pathology. The pathologist then samples the bulk tumor in a few locations and images a stained section under a microscope to determine if the surgeon has completely removed all of cancer cells from the patient. Should the pathologist find a portion of the stained sample with cancer cells bordering ink (a diagnostic known in the medical realm as "positive margin"), the surgeon may be instructed to resect more tissue. However this pathology exercise is a time intensive procedure and often takes days for final results to be sent to the physician. Should a pathology report requiring additional resection return after the patient has completed the initial surgery, this may require the surgeon to perform a second surgery.

In addition to determining clean margins, some surgeries involving the removal of cancerous tissue adjacent to vital tissue structures, such as neurovascular bundles, require precise localization of abnormal tissue to remove the necessary amount of abnormal tissue while avoiding these vital tissue structures as much as possible. Surgeries that require such precise, real-time localization, may include ovarian cancer debulking, brain cancer resection, sarcoma resection, open prostate tumor resection, esophageal cancer resection, and open colo-rectal tumor resection, among others. In the case of ovarian cancer debulking, survival rates correlate directly with the amount of residual cancer left in the wound. A patient is deemed "optimally" debulked if no tumor features larger than 1 cm remain at the end of surgery. With ovarian cancer debulking surgery, 83% of the time, cancer remains in the patient, and of those cases, 50% require reexcision surgeries.

Recent advances have been made for in situ observation of residual cancer cells in a tumor resection bed. See, for example, U.S. Patent Application publication numbers 2009/0299196, 2011/0100471 and 2012/0150164, the disclosures of which are incorporated herein by reference in their entirety. The present application is directed to a hand-held device and related technology for performing such in situ observation of residual cancer cells in a tumor resection bed.

SUMMARY

In one embodiment, a handheld medical imaging device may include a photosensitive detector comprising a plurality of pixels and a rigid imaging tip optically associated with the photosensitive detector. The rigid imaging tip may include a distal end defining a focal plane at a fixed focal distance relative to the photosensitive detector, and the distal end of the rigid imaging tip may be constructed to be placed in contact with tissue and maintain the tissue at the focal plane.

In another embodiment, a hand held medical imaging device may include an imaging device body and a rigid imaging tip distally extending from the imaging device body. A distal end of the rigid imaging tip may define a focal plane with a field of view with a lateral dimension between about 10 mm to 50 mm inclusively. The rigid imaging tip may also include a proximal portion and a distal portion that is angled by about 25° to 65° inclusively relative to the proximal portion. A length of the distal angled portion may be between about 10 mm to 65 mm, and an optical axis may pass through the rigid imaging tip from the distal end of the rigid imaging tip to the proximal end of the rigid imaging tip.

In yet another embodiment, a hand held medical imaging device may include a photosensitive detector comprising a plurality of pixels and a rigid imaging tip optically associated with the photosensitive detector. The rigid imaging tip may include a distal end defining a focal plane relative to the photosensitive detector, and the distal end of the rigid imaging tip may be open. The rigid imaging tip may include at least one opening on a side of the rigid imaging tip that is sized and shaped to provide surgical access to the distal end of the rigid imaging tip.

In another embodiment, a hand held medical imaging device may include a rigid imaging tip including a proximal portion and a distal portion including a distal end. The distal end may include an opening to provide access to a surgical bed and one or more supports extending between the proximal portion and the distal portion. A photosensitive detector may be optically associated with the opening located in the distal end of the rigid imaging tip.

In yet another embodiment, a handheld medical imaging device may include a rigid imaging tip including a distal end defining a field of view and a photosensitive detector optically associated with the rigid imaging tip. A first illumination source may be adapted and arranged to provide light with a first wavelength to the distal end of the rigid imaging tip. A second illumination source may also be adapted and arranged to provide light with a second wavelength to the distal end of the rigid imaging tip. The first wavelength and the second wavelength may be different. Additionally, the first illumination source and the second illumination source may be adapted to alternatingly pulse.

In another embodiment, a handheld medical imaging device may include a rigid imaging tip including a distal end defining a focal plane with a field of view. A photosensitive detector may be optically associated with the rigid imaging tip and an aperture may be located between the photosensitive detector and the rigid imaging tip. The aperture may have a diameter between about 5 mm to 15 mm inclusively. The handheld medical imaging device may also include a first illumination source adapted and arranged to provide between about 10 mW/cm$^2$ to 200 mW/cm$^2$ of light at the focal plane, wherein the light has a first wavelength between about 300 nm to 1,000 nm.

In yet another embodiment, a method for identifying abnormal tissue may include: providing a first light comprising a first excitation wavelength to a surgical bed; collecting a fluorescence signal from the surgical bed using a photosensitive detector; comparing the fluorescence signal to an abnormal tissue threshold to identify abnormal tissue; and indicating one or more locations of the identified abnormal tissue on a screen.

In another embodiment, a method for identifying abnormal tissue may include: illuminating a surgical bed with a first light comprising a first excitation wavelength of a imaging agent using a first illumination source; illuminating the surgical bed with a second light comprising a second wavelength different from the first excitation wavelength using a second illumination source; and collecting a signal from the surgical bed using a photosensitive detector.

In yet another embodiment, a method for identifying abnormal tissue may include: illuminating the surgical bed with ambient light; illuminating a surgical bed with a first light comprising a first excitation wavelength of an imaging agent by pulsing a first illumination source; collecting a first signal from the surgical bed corresponding to ambient light using a photosensitive detector including a plurality of pixels; and collecting a second signal from the surgical bed corresponding to ambient light and a pulse of the first illumination source.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 2A is a schematic side view of a closed tip handheld medical imaging device;

FIG. 2B is a schematic rear perspective view of the closed tip handheld medical imaging device of FIG. 2A;

FIG. 2C is a schematic side perspective view of the closed tip handheld medical imaging device of FIG. 2A;

FIG. 8A is a schematic rear perspective view of a light box;

FIG. 8B is a schematic side view of the light box of FIG. 8A;

FIG. 8C is a schematic perspective view of the light box of FIG. 8A;

FIG. 8D is a schematic cross sectional view of the light box of FIG. 8A;

DETAILED DESCRIPTION

Figure 1A:
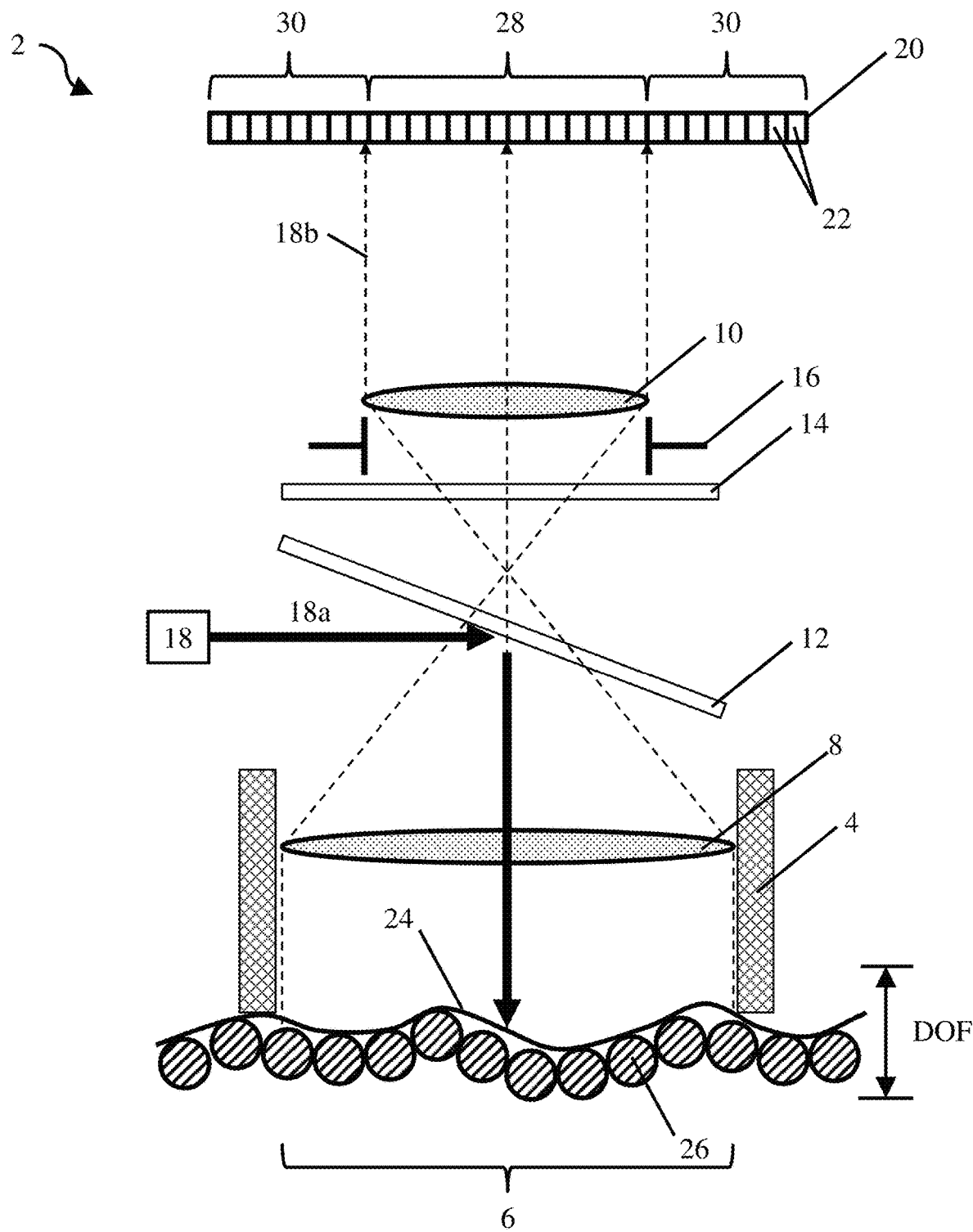
FIG. 1A is a schematic representation of a surgical bed being imaged with decreased magnification.

The inventors have recognized that advances in cancer targeting molecular imaging agents have enabled the detection of small clusters of residual cancer on a background of healthy tissue. However, visually identifying cancerous tissue on the millimeter to submillimeter scale during a surgery is difficult even with these imaging agents. Therefore, the inventors have recognized a need for medical imaging devices capable of reliably detecting millimeter to sub millimeter residual cancer cells during surgery to facilitate the removal of this cancerous tissue. Such an imaging device may help to reduce the number of required follow-up surgeries due to cancerous tissue being left within a surgical bed.

In view of the above, the inventors have recognized the benefits associated with a handheld medical imaging device for use with an appropriate imaging agent. In some embodiments, the medical imaging device may provide sufficient illumination of an excitation wavelength of the imaging agent to generate a fluorescence signal from the imaging agent that exceeds instrument noise of the imaging device. In some embodiments, the illumination provided by the medical imaging device may also result in an autofluorescence signal from healthy tissue. The medical imaging device may also detect abnormal tissue at sizes ranging from centimeters to single cells with sizes on the order of 10 micrometers to tens of micrometers. Other size scales are also possible. As described in more detail below, in some embodiments, it may be desirable for the medical imaging device to be able to image a large field of view in real-time and/or be relatively insensitive to human motions inherent in a handheld device as well as natural motions of a patient involved in certain types of surgery such as breast cancer and lung cancer surgeries. The imaging device may either be used for imaging surgical beds, such as tumor beds, or it may be used for imaging already excised tissue as the disclosure is not so limited.

In one embodiment, a medical imaging device may include a rigid imaging tip including a distal end defining a focal plane at a fixed distance from an optically associated photosensitive detector. For example, a distally extending member may define at its distal end a focal plane of the photosensitive detector. Depending on the embodiment, optics associated with the photosensitive detector may either fix a focus of the photosensitive detector at the focal plane located at the distal end of the rigid imaging tip, or they may permit a focus of the photosensitive detector to be shifted between the focal plane located at the distal end of the rigid imaging tip and another focal plane located beyond the distal end of the rigid imaging tip. While any appropriate photosensitive detector might be used, exemplary photosensitive detectors include a charge-coupled device (CCD) detector, a complementary metal-oxide semiconductor (CMOS) detector, and an avalanche photo diode (APD). The photosensitive detector may include a plurality of pixels such that an optical axis passes from the focal plane of the rigid imaging tip to the photosensitive detector.

Depending on the embodiment, a medical imaging device can also include one or more light directing elements for selectively directing light from an illumination source comprising an excitation wavelength of an imaging agent towards a distal end of the device while permitting emitted light comprising an emission wavelength of the imaging agent to be transmitted to the photosensitive detector. In one aspect, a light emitting element comprises a dichroic mirror positioned to reflect light below a wavelength cutoff towards a distal end of an associated imaging tip while permitting light emitted by the imaging agent with a wavelength above the wavelength cutoff to be transmitted to the photosensitive detector. However, it should be understood that other ways of directing light towards a distal end of the device might be used including, for example, fiber optics, LED's located within the rigid tip, and other appropriate configurations.

An imaging device may also include appropriate optics to focus light emitted from within a field of view of the device onto a photosensitive detector with a desired resolution. In order to provide the desired resolution, the optics may focus the emitted light using any appropriate magnification onto a photosensitive detector including a plurality of pixels. In some embodiments, the magnification is such that each pixel may have a field of view that corresponds to a single cell or only a portion of a single cell. Depending on a size of the individual pixels, the optics may either provide magnification, demagnification, or no magnification as the current disclosure is not so limited. For example, in an embodiment where the pixels of a photosensitive detector are smaller than the cells being imaged, the optics may demagnify the device's field of view to provide a desired field of view for each pixel such as for example 4 pixels per cell. While embodiments in which a field of view of each pixel is equal to or less than a single cell described above, embodiments in which the field of view of each pixel is larger than a single cell are also contemplated.

Without wishing to be bound by theory, a typical cancer cell may be on the order of approximately 15 µm across. In view of the above, an optical magnification of the optics within a medical imaging device may be selected such that a field of view of each pixel may be equal to or greater than about 1 µm, 2 µm, 3 µm, 4 µm, 5 µm, 10 µm, 15 µm, 30 µm, or any other desired size. Additionally, the field of view of each pixel may be less than about 100 µm, 50 µm, 40 µm, 30 µm, 20 µm, 10 µm, or any other desired size scale. In one specific embodiment, the field of view per pixel may be between about 5 µm and 100 µm inclusively. In another embodiment, the field of view per pixel may be between about 5 µm and 50 µm inclusively.

In some instances, it may be desirable to identify both small regions of abnormal tissue as well as larger regions of abnormal tissue. This may be of particular benefit in surgeries such as ovarian cancer surgery where a surgical cavity may have a diameter of 20 cm. Therefore, in one embodiment, optics present within the imaging device may be used to alter a magnification of the emitted light captured by the photosensitive detector between a higher magnification setting used to detect micrometer scale abnormal tissues as well as a lower magnification setting where the medical imaging device may be used in a standoff mode to observe large portions of a surgical cavity. Depending on the embodiment, a field of view of the pixels of a photosensitive detector may be selectively set between about 5 µm and 100 µm. In instances where the medical imaging includes a rigid imaging tip defining a fixed focal plane at a fixed distance from an associated photosensitive detector, the above embodiment may correspond to shifting the focus of the photosensitive detector from the fixed focal plane to a second focal plane located at a second distance beyond the distal end of the rigid imaging tip to enable use of the device in a standoff mode for imaging tissue located beyond the end of the medical imaging device. This second focal plane may either be located at a fixed distance, or it may be variably set using an appropriate focusing element. Further, the focus of the medical imaging device may either be controlled automatically or it may be controlled manually as the disclosure is not limited in this fashion.

As noted above, it may be desirable to improve the resolution and decrease the sensitivity of the medical imaging device to natural motions of a patient during surgery. This may be of particular benefit in surgeries such as breast lumpectomies and lung cancer surgeries where natural movements of the patient may interfere with imaging. Without wishing to be bound by theory, one way to improve resolution and decrease sensitivity to natural motions of a patient is to fix a distance between the tissue being examined and the photosensitive detector being used to capture signals from that tissue. Therefore, in embodiments, the medical imaging device may be adapted and arranged to provide a fixed distance between tissue being examined and the photosensitive detector. This might be provided in any number of ways including, for example, by constructing the rigid imaging tip such that it may be placed in contact with the tissue being examined. The imaging tip may be sufficiently rigid such that it may be pressed against the tissue while retaining its shape. Therefore, the rigid imaging tip may act as a spacer to provide a fixed distance between the tissue and the photosensitive detector. Additionally, since the rigid imaging tip may be pressed against the tissue being examined, it may resist both lateral and out of plane movements of the tissue due to patient movements.

In one embodiment, a rigid imaging tip may correspond to a closed imaging tip. In such an embodiment, a distal end of the rigid imaging tip may be a substantially flat window, such that it defines a focal plane of an associated photosensitive detector. Without wishing to be bound by theory, when the flat surface of the distal end is pressed against tissue being imaged, the tissue may be compressed to conform to a shape of the closed imaging tip. This in turn may position the tissue adjacent to the focal plane of the photosensitive detector to provide a fixed distance between the tissue being examined and the photosensitive detector. In one particular embodiment, the flat distal end may correspond to a flat window disposed on, or integrated into, a distal end of the rigid imaging tip. The window may be transparent to one or more preselected wavelengths, or spectrum of wavelengths, such as an excitation wavelength and emission wavelength of a desired imaging agent. Thus, tissue may be positioned in, or proximate next to, a desired focal plane while permitting light comprising an excitation wavelength and/or emission wavelength of the imaging agent to pass out of and back into the imaging device. In another embodiment, the distal end of the imaging tip may be a ring defining a circular opening and focal plane though other shapes might be used as well.

To facilitate insertion of a rigid imaging tip into a surgical cavity, in some embodiments, it may be desirable for the rigid imaging tip to include a distal portion that is angled relative to a proximal portion of the rigid imaging tip or relative to the body of the hand held device. An optical path of the device may pass from a distal end of the rigid imaging tip through both the distal and proximal portions of the rigid imaging tip to an optically associated photosensitive detector. In order to bend the optical path around the angled distal and proximal portions, the rigid imaging tip may include an appropriate optical component located between the proximal portion and the distal portion of the rigid imaging tip, such as a mirror or prism, that is adapted to bend the optical path around the angled portion of the rigid imaging tip. In one specific embodiment, the rigid imaging tip may have a distal end defining a focal area with a lateral dimension of about 10 mm to 50 mm inclusively, 15 mm to 35 mm inclusively, 25 mm to 35 mm inclusively, or any other appropriate range of dimensions. The distal portion of the tip is also angled relative to the proximal portion by an angle of between about 25° to 65° inclusively, 35° to 55° inclusively, or any other appropriate angle. Additionally, the distal portion of the rigid imaging tip may have a length along the optical path that is about 10 mm to 65 mm inclusively, 25 mm to 65 mm inclusively, or any other appropriate length. Such an embodiment may be particularly suited for use in breast surgeries, whereby the device can be rotated by hand to easily position the focal plane relative to the surgical bed.

In other embodiments, it may be desirable to facilitate imaging of a surgical bed, and simultaneous surgical access. In one such embodiment, the rigid imaging tip may include a distal end including an opening defining the focal plane, that is adapted to be positioned adjacent to tissue during use. The imaging tip may also include one or more openings located on a side of the rigid imaging tip to provide access to the opening in the distal end of the rigid imaging tip. The one or more openings on the side of the imaging tip may either be formed in a sidewall of the rigid imaging tip or between one or more supports extending from a proximal portion of the rigid imaging tip to a distal, tissue-engaging portion of the rigid imaging tip. In one embodiment, the distal ring defining the focal plane is supported by a single strut, and the opening defined by the ring is accessible from any side, being obstructed only by the single strut. In such cases, a surgeon may be able to both image abnormal tissue located within a field of view of the rigid imaging tip as well as simultaneously perform surgery on the identified abnormal tissue through the open distal end and the one or more side openings of the rigid imaging tip.

In embodiments, the medical imaging device may be associated with and/or coupled to one or more illumination sources. For example, a first illumination source may be adapted and arranged to provide light including a first wavelength to a light directing element that reflects light below a threshold wavelength towards a distal end of a rigid imaging tip and transmits light above the threshold wavelength. However, other ways of directing light from the one or more illumination sources toward the distal end of the rigid imaging tip including fiber optics and LED's located within the device or rigid imaging tip might also be used. Regardless, or how the light is directed, the first wavelength may be selected such that it is below the threshold wavelength and thus will be reflected towards the distal end of the rigid imaging tip to illuminate the device's field of view. The illumination source may either be a constant illumination source or a pulsed illumination source depending on the particular embodiment. Additionally, the first wavelength may be selected such that it corresponds to an excitation wavelength of a desired imaging agent. It should be understood that the specific wavelength will be dependent upon the particular imaging agent, optics, as well as the sensitivity of the photosensitive detector being used. However, in one embodiment, the first wavelength may be about 300 nm to 1,000 nm, 590 nm to 680 nm, 600 nm to 650 nm, 620 nm to 640 nm, or any other appropriate range of wavelengths depending on the particular imaging agent being used. Additionally, the first illumination source may be adapted to provide between about 10 mW/cm$^2$ to 200 mW/cm$^2$ at a desired focal plane for imaging tissue within a surgical bed, though other illumination intensities might also be used. For example, a light intensity of 50 mW/cm$^2$ to 200 mW/cm$^2$, 100 mW/cm$^2$ to 200 mW/cm$^2$, 150 mW/cm$^2$ to 200 mW/cm$^2$ could also be used. Depending on the particular imaging agent being used, the various components of the medical imaging device may also be constructed and arranged to collect emission wavelengths from an imaging agent that are about 300 nm to 1,000 nm, 590 nm to 680 nm, 600 nm to 650 nm, 620 nm to 640 nm, or any other appropriate range of wavelengths.

In order to help reduce spherical aberrations and improve a depth of field of an image, a medical imaging device may include an appropriately sized aperture. However, smaller aperture sizes result in correspondingly lower signals reaching an associated photosensitive detector. Therefore, depending on the signal magnitude of an imaging agent versus an autofluorescence signal of surrounding normal tissue as well as the photosensitive detector ground and dark noise, it may be necessary to increase the illumination provided by an associated illumination source. In one embodiment, an appropriate combination of aperture size and illumination source include an illumination source as noted above and an aperture located between the photosensitive detector and the rigid imaging tip with a diameter between about 5 mm to 15 mm inclusively to provide an image side f number between about 1.5 to 4.5 inclusively. In a related embodiment, the aperture might be sized to provide an f number between about 3 to 3.5 inclusively.

In one specific embodiment, an imaging device includes an aperture with a width of about 10.6 mm corresponding to an image side f number of about 3.4. The imaging device also includes a light source including a 50 W red LED adapted to emit about 5 W of light at 630 nm. In this embodiment, the light incident on a surgical bed is about 60 mW/cm$^2$. The associated light directing element is a dichroic mirror with a wavelength cutoff threshold of about 660 nm that reflects light with wavelengths less than that cutoff threshold towards a distal end of the imaging device. While a particular aperture, cutoff threshold, and illumination source are described above, it should be understood that other ranges of aperture sizes, f numbers, wavelengths, and cutoff thresholds are also contemplated as previously discussed.

In some instances, in order to facilitate surgery while imaging a surgical site, it may be desirable to enable imaging of objects and/or healthy tissue in addition to abnormal tissue marked with an imaging agent within a surgical site. In such an embodiment, an imaging device may include a second illumination source constructed and arranged to provide light to the surgical site. In one embodiment, the second illumination source may simply be ambient light incident on a surgical site due to an imaging device being operated in a standoff mode where it is not in contact with the tissue or from the device including openings through which the ambient light may enter. In another embodiment, a second illumination source may provide light with one or more wavelengths, or a spectrum of wavelengths, that are greater than a cutoff wavelength of the light directing element and an associated excitation wavelength of the imaging agent. Therefore, light from the second illumination source may illuminate tissue located within a field of view of the device and pass through the light directing element towards an associated photosensitive detector. This may help to generate "white light" images during use. The first illumination source corresponding to an excitation wavelength of the imaging agent may either be operated in a constant mode or it may be pulsed during imaging to facilitate isolating the florescence signal as described in more detail below.

Without wishing to be bound by theory, in some instances, identifying a fluorescence signal from abnormal tissue marked with an imaging agent from autofluorescence signals emitted from surrounding healthy tissue may be difficult. For example, an emission signal from a marked abnormal tissue may become convoluted with an autofluorescence signal making it more difficult to identify. Some types of tissue that are known to generate large fluorescence signals that might interfere with identification of residual cancer during intraoperative imaging may include, but are not limited to, tissues such as bone and skin. Hence, a system that can isolate a fluorescence signal that arises from a cancer-targeting imaging agent from a background fluorescence signal that arises due to native fluorescent agents may be advantageous.

In one embodiment, mitigating interference from autofluorescence of tissue within a surgical site may involve the use of a first illumination source and a second illumination source coupled to a medical imaging device. The first and second illumination sources may either be separate devices, or they may be combined as noted above. The medical imaging device may include a distally extending imaging tip where a distal end of the imaging tip defines a field of view of the device. The first illumination source and the second illumination source may be coupled to the imaging device such that they provide light to the distal end of the imaging tip. For example, a dichroic mirror may be positioned along an optical path such that it directs light from the first and second illumination sources to the distal end of the imaging tip. Alternatively, other methods of directing light from the first and second illumination sources towards the distal end of the imaging might also be used as described above. The first illumination source may produce a first light with a first wavelength that corresponds to an excitation wavelength of a desired imaging agent. The second illumination source may produce a second light with a second wavelength corresponding to a different excitation wavelength of the desired imaging agent. Additionally, the first illumination source and the second illumination source may alternatingly pulse to induce different fluorescence signals from tissue located within the field of view. Depending on the embodiment, the first and second illumination sources may alternatingly pulse for each exposure period of a photosensitive detector or each pulse may last for multiple exposures of a photosensitive detector as the disclosure is not so limited.

In embodiments where two or more illumination sources are used, the illumination sources may correspond to either a single illumination source or multiple illumination sources as the disclosure is not so limited. For example, a single illumination source might provide light including multiple wavelengths. Filters and other appropriate optical components could then be used to provide the separate desired wavelengths of light to the appropriate locations on the medical imaging device.

Without wishing to be bound by theory, an imaging agent separately exposed to two different excitation wavelengths will exhibit a predictable rise or drop in the resulting fluorescence signal intensity. Therefore, a change between the fluorescence signals captured by a pixel of a photosensitive detector in response to excitation from two separate illumination sources may be compared to the expected change in the fluorescence signal for the imaging agent to identify abnormal tissue marked by the imaging agent. Conversely, pixels that do not exhibit the expected change in the fluorescence signal may be identified as normal tissue. For example, when LUM015 is used to mark a desired tissue, a first excitation wavelength between about 590 nm and 670 nm as well as a second excitation wavelength of between about 510 nm and 590 nm might be used. LUM015 includes the fluorochrome CY5 and is described generically in U.S. Publication Number 2011/0104071 and also in U.S. application Ser. No. 61/781,601, the disclosures of which are incorporated herein by reference. LUM033 also includes the fluorochrome CY5 and can likewise be used to mark a desired tissue, using the same first excitation wavelength of between about 590 nm and 670 nm and second excitation wavelength of between about 510 nm and 590 nm. Lum 33 also is described generically in U.S. Publication Numbers 2011/0104071 and 2012/0150164. It is similar to LUM015 in that it has a pharmacokinetic modifier and a Cy5 fluorochrome, but it does not have a quencher and an enzyme cleavage site. Instead, it relies on a pharmacokinetic modifier that clears the imaging agent preferentially from the healthy tissue leaving the cancer cells and/or tumor associated inflammation cells labeled. It should be understood that appropriate excitation wavelengths will vary for different imaging agents and that the disclosure in some aspects is not limited to any particular first and second excitation wavelengths.

As noted previously it may be desirable to provide approximately 2 mm tumor margins that are free of residual cancer cells. Therefore, in some embodiments, it may be beneficial to use an imaging agent that provides a detection depth on the order of about 1 mm to 2 mm from the surgical bed surface to provide for imaging of cells located at the surgical bed surface to the desired detection depth of about 1 mm to 2 mm. Without wishing to be bound by theory, by selecting an imaging agent with appropriate excitation and fluorescence emission wavelengths, the penetration depth of the imaging agent may be limited to a desired range such as about 1 mm to 2 mm inclusively as noted above. Therefore, a surgeon may be confident that the detected signal corresponds to tissue located within about 1 mm to 2 mm from the surgical bed surface. This enhanced depth specificity may enable a surgeon to resect a smaller amount of tissue which is beneficial for multiple reasons. Again, without wishing to be bound by theory, light with wavelengths in the far red spectrum corresponding to wavelengths of about 710 nm to 850 nm may offer penetration depths of about 1 mm to 2 mm in tissue, though wavelengths between about 300 nm and 1,000 nm could also be used. Consequently, imaging agents that operate in the far red spectrum may provide the desired penetration depths of about 1 mm to 2 mm from a surgical bed surface. Therefore, in some embodiments, a medical imaging device may be used with an imaging agent that operates in the far red spectrum. However, it should be understood that an imaging agent may provide a detection depth that is either larger or smaller than 2 mm as the disclosure is not so limited. For example, imaging agents with excitation and fluorescence emission wavelengths capable of providing detection depths between about 1 mm to 5 mm might also be used. It should be understood that excitation wavelengths with penetration depths greater than the desired penetration depth might be used since the emitted fluorescence signal would still be limited to the desired penetration depth. Therefore, for example, a device might be operated with an imaging agent with an excitation wavelength at one wavelength and a separate fluorescence wavelength between about 590 nm and 850 nm.

An exemplary imaging agent capable of providing the desired detection depths noted above is LUM015 (and other such agents described in U.S. Patent Publication Number 2011/0104071) which employ the fluorophore CY5. Other appropriate fluorophores that might be included in an imaging agent include, but are not limited to, Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red. Of course, one of ordinary skill in the art will be able to select imaging agents with fluorophores suitable for a particular application.

The Lum Imaging agents presently used are the subject of patent application Ser. No. 14/211,014, now U.S. Pat. No. 9,763,577, and entitled IMAGING AGENT FOR DETECTION OF DISEASED CELLS, the disclosure of which is incorporated herein by reference.

In view of the desired detection depths, an imaging device may be optimized to take into account both the desired imaging depth as well as anticipated natural movements of a patient during surgery. For example, movements of the chest during lung cancer and breast lumpectomy surgeries are to be expected. Consequently, the depth of field of an imaging device may be between about 0.1 mm and 10 mm inclusively, 0.1 mm to 5 mm inclusively, or 1 mm to 5 mm inclusively. However, it should be understood that other depths of field both larger and smaller than the ranges noted above are also contemplated.

The medical imaging devices described herein may be used in any number of ways. However, in one embodiment, the medical imaging device may be used to identify abnormal tissue located within a surgical bed. This may include providing a first light including a first excitation wavelength of a desired imaging agent to the surgical bed. The first excitation wavelength may result in a fluorescence signal being emitted from abnormal tissue marked with an appropriate imaging agent such as, for example, LUM015. An appropriate photosensitive detector including a plurality of pixels may collect the emitted fluorescence signal for comparison to an abnormal tissue threshold. Pixels collecting fluorescence signals greater than the abnormal tissue threshold may be identified as corresponding to abnormal tissue.

Depending on the particular embodiment, an abnormal tissue threshold may be determined in a number of ways. In instances where the fluorescence signal associated with surrounding healthy tissue and a particular marked abnormal tissue is well-established, the abnormal tissue threshold might simply correspond to a predetermined number corresponding to that type of abnormal tissue marked with a particular imaging agent. For example, the abnormal tissue threshold may be $16.6 \times 10^{10}$ counts/s/cm$^2$ for breast cancer surgery performed using LUM015. In contrast, in instances where autofluorescence signals and fluorescence signals of a marked abnormal tissue may vary widely between individuals, an abnormal tissue threshold may be determined by first measuring a normal tissue signal on a healthy section of tissue. An abnormal tissue threshold may then be defined as having a signal intensity that is greater than the normal tissue signal by a predetermined value. For example, a surgeon might image a section of normal tissue and a controller of the imaging device may analyze the image to both determine a normal tissue signal and an appropriate abnormal tissue threshold. This may be of particular benefit in instances where an imaging device collects both fluorescence signals from an imaging agent as well as autofluorescence signals from tissue within a surgical bed.

In addition to the above, in some embodiments a medical imaging device may also include a size threshold for determining if a fluorescent signal that is greater than an abnormal tissue threshold is statistically significant. This may help to identify whether or not an abnormal tissue marked with an imaging agent is present or if abnormal tissue larger than a desired size is present. For example, a controller of a medical imaging device may identify one or more contiguous pixels exhibiting a fluorescence signal greater than an abnormal tissue threshold. However, if a size of the identified one or more contiguous pixels is less than a size threshold, the controller may disregard this signal as being statistically insignificant and will not identify the tissue as being abnormal tissue. For example, if a size of a region exhibiting a fluorescence signal is less than the size of a cell, a system may determine that the detected signal is not associated with abnormal tissue. Alternatively, it may only be desirable to remove portions of abnormal tissue that are above a certain size threshold for practical reasons such as limited surgical time. Therefore, depending on the particular application, an appropriate size threshold may be less than a size of a single cell or multiple cells as the current disclosure is not so limited. For instance, an appropriate size threshold may be between about 5 μm to 160 μm, 5 μm to 100 μm, or 5 μm to 50 μm. Other size thresholds both greater than and less than those noted above are also contemplated and will depend on the particular imaging agent and tissue being examined.

As described above, a controller associated with a medical imaging device may process the collected raw images to identify the presence of abnormal tissue within a field of view of the device using appropriate signal and/or size thresholds. In addition to determining the presence of abnormal tissue within a field of view, the controller may also output the collected images to a screen, or other viewing device for viewing by a user. The controller may then specifically indicate the location(s) of the previously identified abnormal tissue on the screen in order to bring them to a surgeon's attention. The location(s) of the identified abnormal tissue may be indicated on the screen in any appropriate manner including, for example, highlighting the locations of the identified abnormal tissue and/or a perimeter of the identified abnormal tissue using an appropriate color, increased contrast, increased intensity, or other appropriate way of highlighting the desired features on a screen or output device. Alternatively, geometric shapes superimposed onto the image might be used to indicate the location of identified abnormal tissue on a screen or other output device. Appropriate geometric shapes may include, but are not limited to, an arrow, or other shape, pointing to the identified abnormal tissue or a shape such as a circle, a square, a rectangle, a non-symmetric closed loop, or other appropriate shape superimposed onto the screen such that it encompasses a perimeter of the identified abnormal tissue. In some embodiments, highlighting might be used to indicate abnormal tissue with a size greater than a predetermined size limit and geometric shapes might be used to indicate abnormal tissue with a size less than the predetermined size limit. In some embodiments, both highlighting and geometric shapes are used to indicate the location of identified abnormal tissue with a size that is less than a predetermined size limit. Depending on the particular use, the predetermined size limit may be less than about 1 mm$^2$, 2 mm$^2$, 3 mm$^2$, 4 mm$^2$, or any other appropriate dimension. Therefore, it should be understood that other predetermined size limits both greater than and less than those noted above are also possible. Other ways of indicating the location of abnormal tissue are also possible. While specific ways of indicating the presence of identified abnormal tissue on a screen or other output device are described above, the disclosure is not limited to the specific embodiments described herein and should instead be interpreted as encompassing any appropriate method of indicating the presence of abnormal tissue on a screen or other output device.

While various combinations of optical components and illumination sources are described above and in reference to the figures below, it should be understood that the various optical components such as filters, dichroic mirrors, fiber optics, mirrors, prisms, and other components are not limited to being used with only the embodiments they are described in reference to. Instead these optical components may be used in any combination with any one of the embodiments described herein.

Turning now to the figures, several specific embodiments are described in more detail. It should be understood that the specific features described in regards to the various embodiments are not limited to only those embodiments. Instead, the various embodiments and features may be combined in various ways as the disclosure is not limited.

Figure 1B:
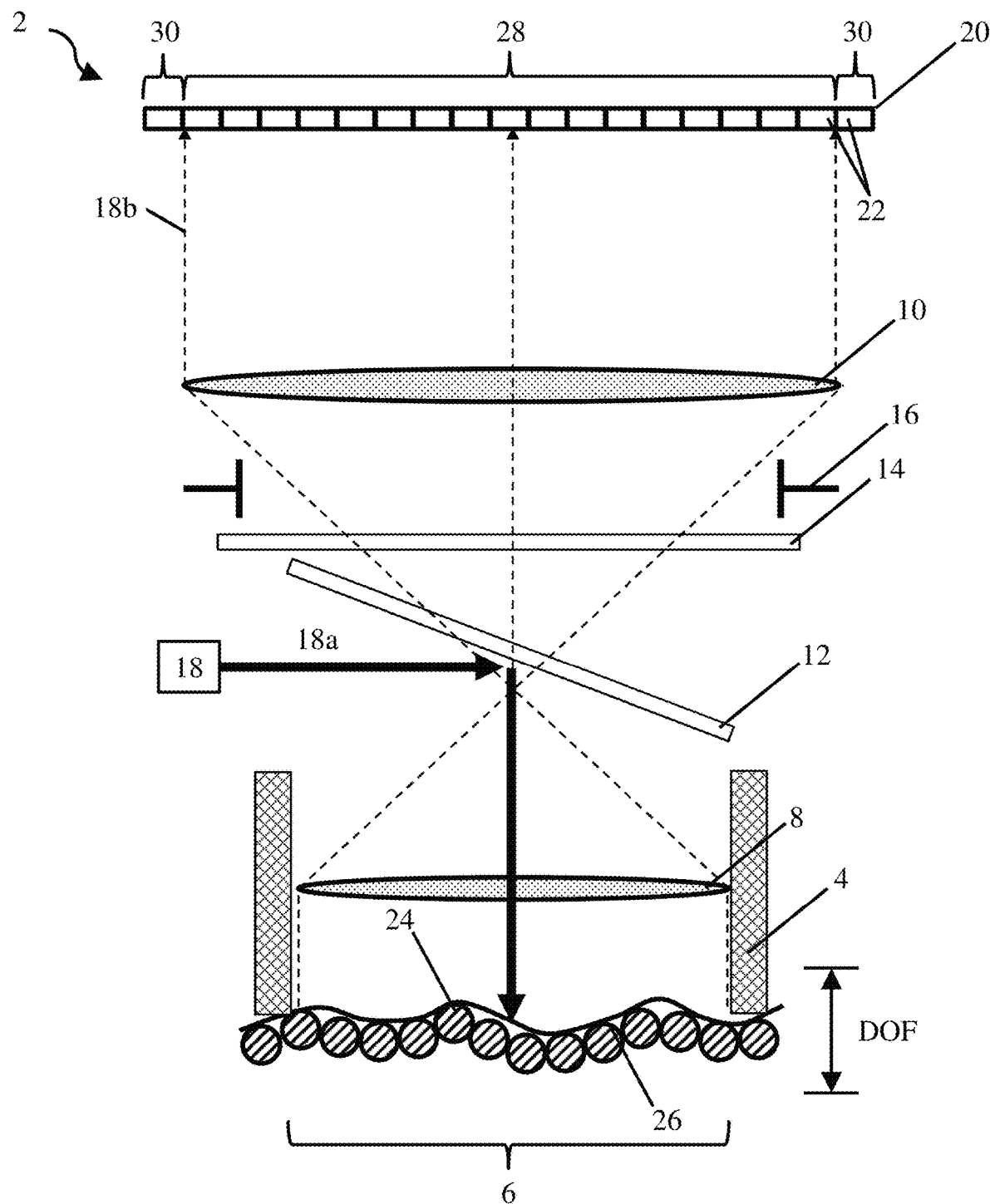
FIG. 1B is a schematic representation of a surgical bed being imaged with increased magnification.
Figure 3A:
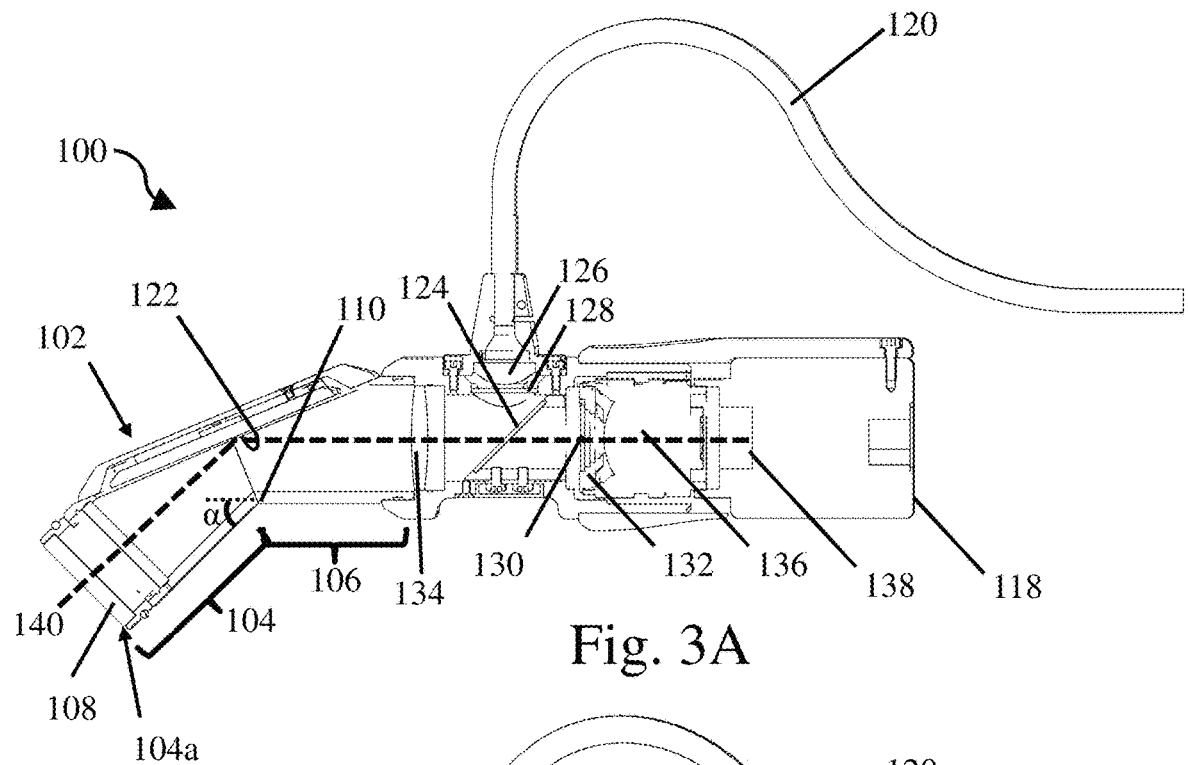
FIG. 3A is a cross sectional view of the closed tip handheld medical imaging device of FIG. 2A.
Figure 3B:
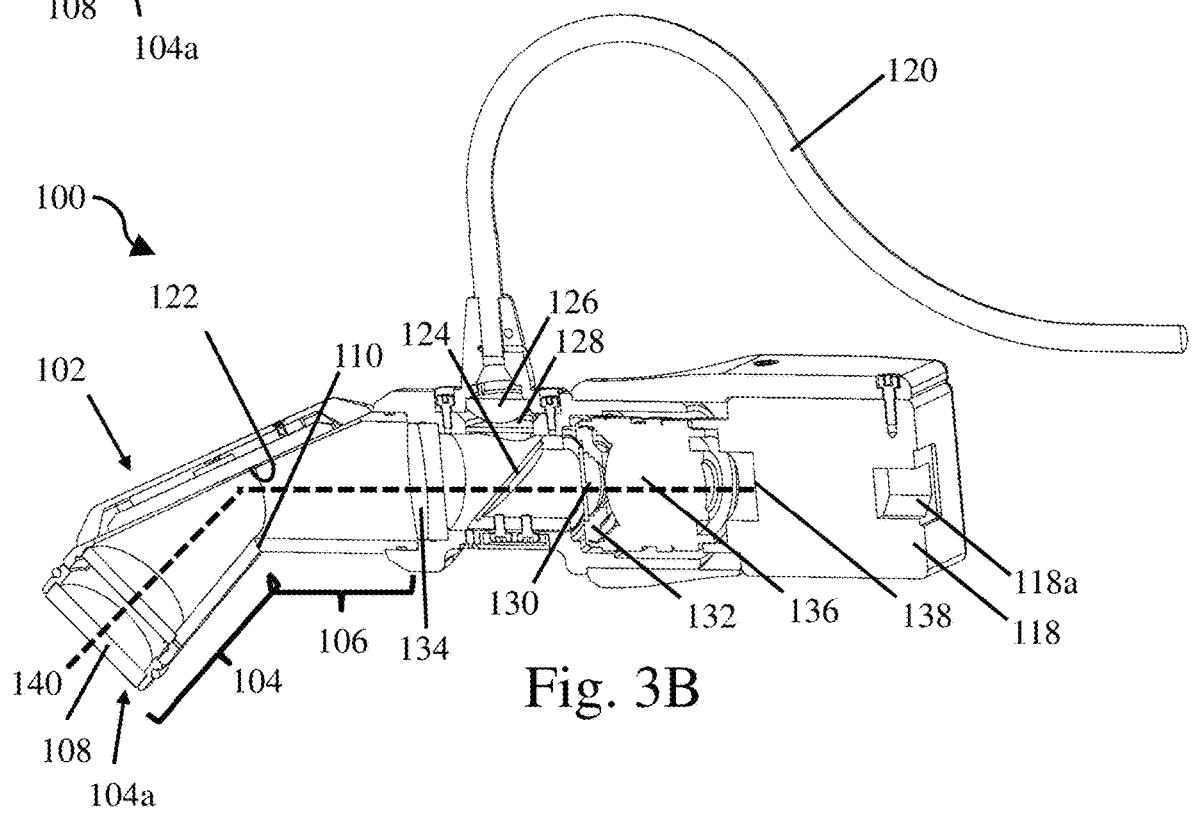
FIG. 3B is perspective cross sectional view of the closed tip handheld medical imaging device of FIG. 2A.
Figure 4C:
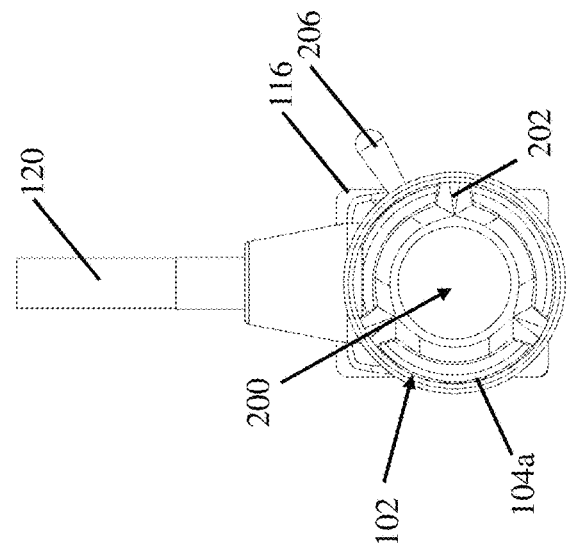
FIG. 4C is a schematic front perspective view of the open tip handheld medical imaging device of FIG. 4A.
Figure 4A:
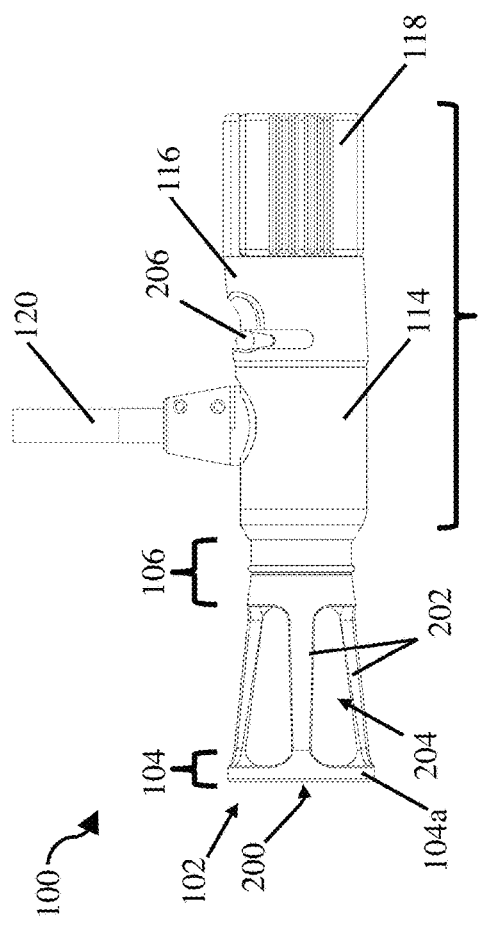
FIG. 4A is a schematic side view of an open tip handheld medical imaging device.
Figure 4B:
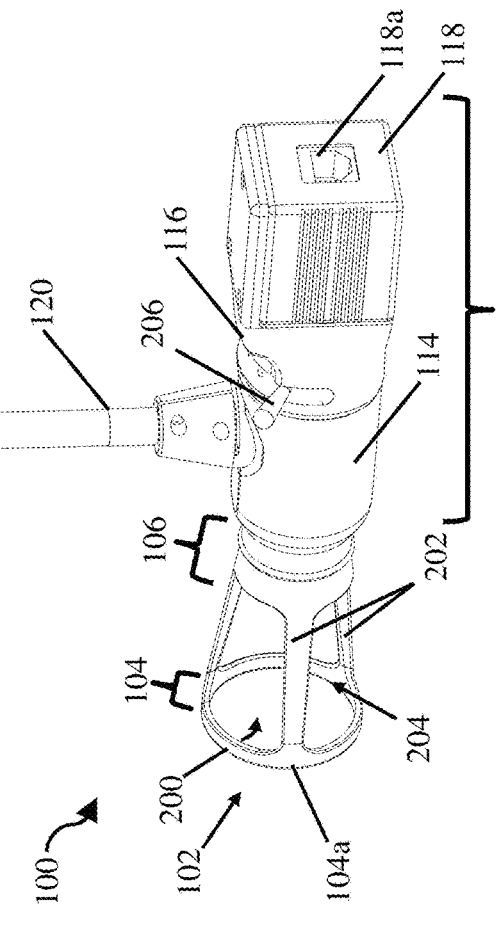
FIG. 4B is a schematic rear perspective view of the open tip handheld medical imaging device of FIG. 4A.
Figure 5A:
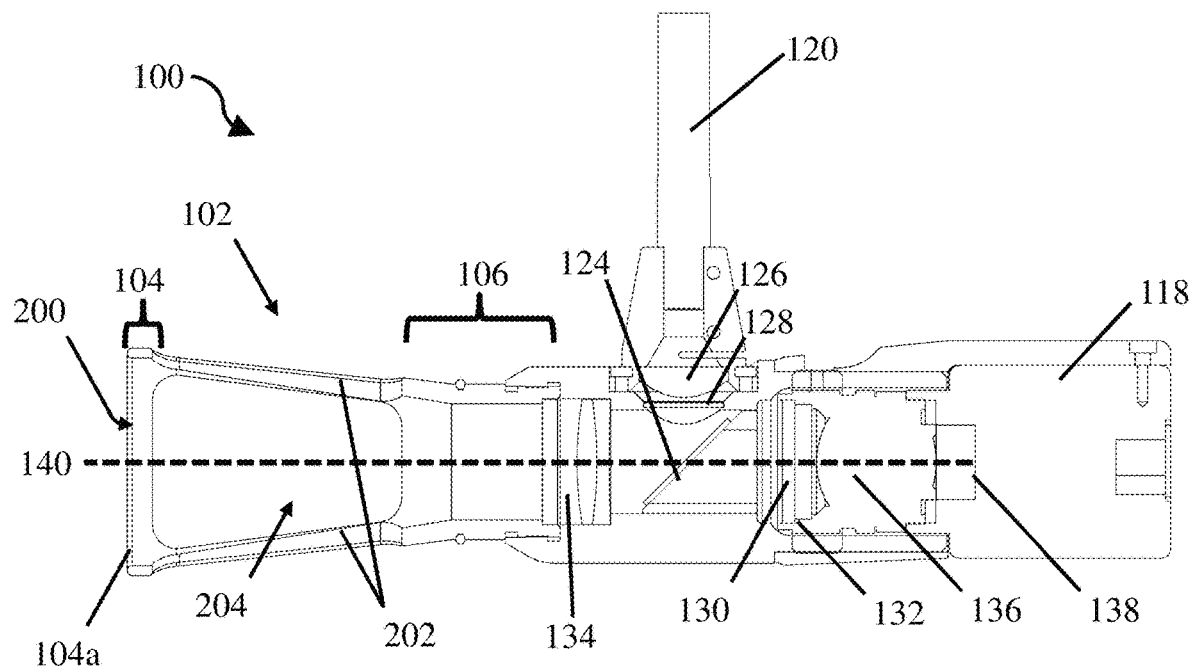
FIG. 5A is a schematic cross sectional view of the open tip handheld medical imaging device of FIG. 4A.
Figure 5B:
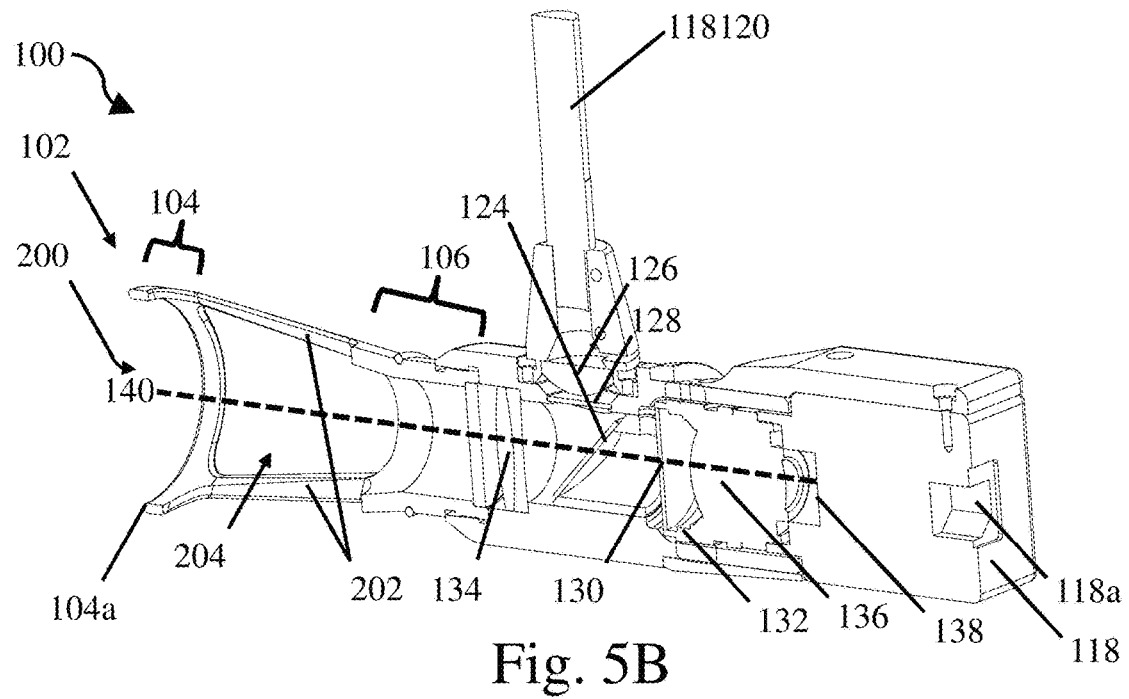
FIG. 5B is perspective cross sectional view of the open tip handheld medical imaging device of FIG. 4A.

FIGS. 1A and 1B depict schematic representations of exemplary embodiments for components of a medical imaging device 2. The medical imaging device may include a rigid imaging tip 4 at least partially defined by a distally extending member, frustoconical cylinder or other hollow structure. The rigid imaging tip 4 may be constructed and arranged to be held against tissue to fix a focal length of the medical imaging device relative to the tissue. As depicted in the figures, the rigid imaging tip 4 may also include an open distal end that defines a field of view 6. The medical imaging device 2 may also include optics such as an objective lens 8, an imaging lens 10, and an aperture 16. The optics may focus light from the field of view 6 onto a photosensitive detector 20 including a plurality of pixels 22. The medical imaging device may also include features such as a light directing element 12 and a filter 14. While a doublet lens arrangement has been depicted in the figures, it should understood that other types of optics capable of focusing the field of view 6 onto the photosensitive detector 20 might also be used including, for example, fiber-optic bundles. Additionally, the photosensitive detector may correspond to a detector such as a CCD, a CMOS array, an APD array, or other appropriate detector.

With regards to the above noted embodiment, appropriate lenses for the objective lens and imaging lens include, but are not limited to, an imaging lens with a focal length between about 8 mm and 75 mm, and an objective lens with a focal length between about 10 mm and 250 mm. For example, in one specific embodiment, an imaging lens has a focal length of 50 mm and an objective lens has a focal length of 40 mm for imaging LUM-1. In another possible embodiment, an imaging lens has a focal length of 200 mm and an objective lens has a focal length of 25 mm for imaging LUM 2.6. It should be understood that other focal lengths for the imaging and objective lenses that are either greater than or less than the ranges noted above are also contemplated.

As illustrated in the figures, the medical imaging device may be positioned such that a distal end of the rigid imaging tip 4 may be pressed against a surgical bed 24 including one or more cells 26 which may be marked with a desired imaging agent. Instances where all, a portion, or none of the cells are marked with the imaging agent are contemplated. Pressing the rigid tip against the surgical bed may prevent out of plane and lateral tissue motion, which may allow for collection optics with larger f numbers and consequently, larger collection efficiencies, smaller blur radii, and smaller depth of field. Additionally, pressing the rigid imaging tip 4 against the surgical bed may provide a fixed focal length between the tissue bed 24 and photosensitive detector 20. In some embodiments, the rigid imaging tip may have a length such that the distal end of the rigid imaging tip is also located at a focal plane of the photosensitive detector 20. Therefore, pressing the rigid imaging tip against the surgical bed may position the surgical bed 24 and the cells 26 contained therein at the focal plane of the imaging device. Depending on the particular embodiment, a distal end of the rigid imaging tip 4 may include a flat surface to help position the surgical bed in the desired focal plane. However, in instances where an end of the rigid imaging tip is open, an appropriate depth of field (DOF) still may be provided to facilitate imaging of the tissue located within the field of view.

In some embodiments, it may be desirable to maintain a fixed distance between a distal end of the rigid imaging tip and the photosensitive detector. This may help to maintain the focus of tissue located within the focal plane defined by the distal end of the rigid imaging tip. Therefore, the rigid imaging tip may be adapted to resist deflection and/or deformation when pressed against a surgical bed such that tissue located within the focal plane defined by the distal end of the rigid imaging tip is maintained in focus. For example, a rigid imaging tip may deflect by less than the depth of field of the medical imaging device in response to forces of about 5 lbf, 10 lbf, 15 lbf, 20 lbf, or any other appropriate force. Appropriate materials for forming the rigid imaging tip include, but are not limited to, polycarbonate, acrylic, and BK7 glass.

During use, the medical imaging device may be associated with an illumination source 18 that directs light 18a with a first wavelength towards the light directing element 12. The first wavelength may correspond to an excitation wavelength of a desired imaging agent. In some instances, the illumination source 18 may include appropriate components to collimate the light 18a. The illumination source 18 might also include one or more filters to provide a desired wavelength, or spectrum of wavelengths, while filtering out wavelengths similar to those detected by the photosensitive detector 20. In some embodiments, the light directing element 12 may be a dichroic mirror with a cutoff wavelength that is greater than the first wavelength. Thus, the light directing element 12 may reflect the incident light 18a towards a distal end of the rigid imaging tip 4 and onto the surgical bed 24. When the one or more cells 26 that are labeled with a desired imaging agent are exposed to the incident light 18a, they may generate a fluorescent signal 18b that is directed towards the photosensitive detector 20. The fluorescent signal may have a wavelength that is greater than the cutoff wavelength of the light directing element 12. Therefore, the fluorescent signal 18b may pass through the light directing element 12. The filter 14 may be a band pass filter adapted to filter out wavelengths other than the wavelength of the fluorescent signal. Alternatively, the filter 14 may permit other selected wavelengths to pass through as well. The fluorescent signal 18b may also pass through an aperture 16 to the imaging lens 10. The imaging lens 10 may focus the fluorescent signal 18b, which corresponds to light emitted from the entire field of view, onto a plurality of pixels 22 of the photosensitive detector 20. In some instances, the fluorescent signal 18b may be focused onto a first portion 28 of the photosensitive detector while second portions 30 of the photosensitive detector are not exposed to the fluorescent signal. However, it should be understood that in some embodiments, the fluorescent signal may be focused on to an entire surface of a photosensitive detector as the disclosure is not so limited.

In some embodiments, a field of view of each pixel of the one or more pixels 22 of the photosensitive detector 20 may be selected such that it is less than or equal to a desired cell size. However, depending on the particular photosensitive detector used, the one or more pixels 22 may either be larger or smaller than a desired cell size. Consequently, and as illustrated by FIGS. 1A and 1B, respectively, a fluorescent signal 18b emitted from a surgical bed may be magnified or demagnified by the imaging device's optics to provide a desired field of view for each pixel 22. Additionally, in some embodiments, the optics may provide no magnification to provide a desired field of view for each pixel 20. For example, in the case of a photosensitive detector including pixels that are smaller than a single cell, an imaging device 2 may provide a magnification factor of about 0.1 to 0.5 inclusively, 0.2 to 0.3 inclusively, or any other appropriate magnification factor to provide a desired number of pixels per cell.

Having generally described embodiments related to a medical imaging device and an associated rigid imaging tip, several specific embodiments directed to different types of rigid imaging tips are described in more detail below with regards to FIG. 2A-5C.

FIGS. 2A-2C and 4A-4C generally depict embodiments of a medical imaging device 100 including a distally extending rigid imaging tip 102 corresponding to a tube with an open inner diameter. The rigid imaging tip 102 may include a distal portion 104 and a proximal portion 106. A distal end 104a of the rigid imaging tip located on the distal portion 104 may define a field of view for the imaging device. Additionally, the proximal portion 106 may be constructed to either be detachably or permanently connected to a body 112 of the imaging device. In embodiments where the proximal portion 106 is detachably connected to the body 112, the connection may include, for example, a snap on, screw on, suction, or magnetic connection. This may provide multiple benefits including, for example, easily and quickly changing a rigid imaging tip during a surgical procedure as well as enabling the rigid imaging tip to be removed and sterilized. Consequently, in some embodiments, the rigid imaging tip may also be made from materials that are compatible with typical sterilization techniques such as various steam, heat, chemical, and radiation sterilization techniques.

Depending on the particular embodiment, a body 112 of a medical imaging device 100 may be constructed and arranged to be a handheld medical imaging device. However, embodiments in which the medical imaging device, and/or the methods of use described herein, are applied to a medical imaging device that is not handheld are also possible. As depicted in the figures, the body 112 may include a light coupling section 114 attached to a housing 116. The housing 116 may be adapted to mount a photosensitive detector 118 to the medical imaging device. In some embodiments, the photosensitive detector 118 may include an appropriate data output 118a for outputting data to an external controller, not depicted. One or more light inputs 120 associated with one or more separate illumination sources, not depicted, may be coupled to the light coupling section 114 as depicted in the figures to provide light including at least a first excitation wavelength to the medical imaging device 100.

Referring now to FIGS. 3A-3B and 5A-5B, the general arrangement of components within a medical imaging device 100 interior are described in more detail. As depicted in the figures, the medical imaging device may include a rigid imaging tip 102 corresponding to a member distally extending from the body 112 with an optically transparent or hollow interior. A distal end 104a of the rigid imaging tip 102 may define a focal plane located at a fixed distance relative to the optically coupled photosensitive detector 118 located on a proximal portion of the medical imaging device. In one embodiment, the optics coupling the rigid imaging tip and the photosensitive detector may include an objective lens 134 and an imaging lens 136 located between the rigid imaging tip and the photosensitive detector. The objective and imaging lenses 134 and 136 may focus light emitted from within a field of view of the rigid imaging tip onto a surface 138 of the photosensitive detector 118 including a plurality of pixels. A magnification provided by the combined objective and imaging lenses 134 and 136 may be selected to provide a desired field of view for each pixel. Again, the field of view for each pixel may be selected such that each pixel may correspond to one cell or less of a tissue being imaged. However, embodiments in which each pixel may correspond to more than one cell are also contemplated.

The medical imaging device 100 may also include one or more light directing elements 124 located between the photosensitive detector 118 and a distal end 104a of the rigid imaging tip. For example, as depicted in the figure, the light directing element 124 may be located between the objective lens 134 and the imaging lens 136. However, other locations within the medical imaging device including along the rigid imaging tip are also contemplated. The light directing element 124 may be adapted to reflect light below a cutoff wavelength towards the distal end of the rigid imaging tip and transmit light above the cutoff wavelength towards the photosensitive detector 118. In the current embodiment, the cutoff wavelength may be greater than an excitation wavelength of a desired imaging agent and less than an emission wavelength of the imaging agent. While any appropriate structure might be used for the light directing element, in one embodiment, the light directing element is a dichroic mirror.

In some embodiments, the medical imaging device 100 may include one or more filters 130 located between the light directing element 124 and the photosensitive detector 118. The one or more filters 130 may be adapted to permit light emitted from an imaging agent to pass onto the photosensitive detector while blocking light corresponding to excitation wavelengths of the imaging agent. Depending on the embodiment, the one or more filters may either permit a broad spectrum of wavelengths to pass or they may only permit the desired emission wavelength, or a narrow band surrounding that wavelength, to pass as the disclosure is not so limited.

An aperture stop 132 including an appropriately sized aperture may also be located between the rigid imaging tip 102 and the photosensitive detector 118. More specifically, the aperture stop 132 may be located between the light directing element 124 and the imaging lens 136. Depending on the embodiment, the aperture may have an aperture diameter selected to provide a desired f number, depth of field, and/or reduction in lens aberrations. Appropriate aperture diameters may range from about 5 mm to 15 mm inclusively which may provide an image side f number between about 3 to 3.5 inclusively. However, other appropriate aperture diameters and f numbers are also contemplated.

During use, a medical imaging device 100 may be coupled to a light input 120 from an associated illumination source. The light input 120 may be any appropriate structure including, for example, fiber-optic cables used to transmit light from an associated illumination source to the medical imaging device. The light input 120 may be associated with optical elements such as an aspheric lens to help collimate light directed towards the light directing element 124. The light input 120 may also be associated with one or more filters in order to provide a desired wavelength, or a spectrum of wavelengths. This wavelength, or spectrum of wavelengths, may correspond to one or more excitation wavelengths of a desired imaging agent used to mark abnormal tissue for imaging purposes. Depending on the particular embodiment, the light input 120 may either be associated with a single illumination source, or it may be associated with multiple illumination sources. Alternatively, multiple light inputs may be coupled to the medical imaging device to provide connections to multiple illumination sources as the current disclosure is not so limited.

It should be understood that the above components may be provided in any desired arrangement. Additionally, a medical imaging device may only include some of the above noted components and/or it may include additional components. However, regardless of the specific features included, an optical axis 140 of a medical imaging device may pass from a distal end 104a of a rigid imaging tip 102 to a photosensitive detector 118. For example, light emitted from within a field of view may travel along an optical path 140 passing through the distal end 104a as well as the distal and proximal portions 104 and 106 of the rigid imaging tip. The optical path may also pass through a light coupling section 114 and housing 116 including various optics to the photosensitive detector 118.

During certain surgical procedures, a surgical site may be subjected to natural movements from a patient such as breathing, the surgical site may present irregular surfaces, and/or sidewalls might be necessary for operation within the surgical cavity. Consequently, in some embodiments a medical imaging device may include a rigid imaging tip with a closed flat distal end that may be pressed against a surgical bed within a surgical site to help mitigate movement of the surgical bed relative to the medical imaging device. However, it should be understood that a closed rigid imaging tip might also be used for other purposes as well. In some embodiments, the medical imaging device may also be shaped and sized to facilitate insertion into a surgical site for specific surgeries. One such embodiment is described in more detail below with regards to FIG. 2A-3B.

As depicted in the figures, a medical imaging device 100 may include a rigid imaging tip 102 with a distal portion 104 and a proximal portion 106. The distal portion 104 may include a distal end 104a including an opening optically associated with a photosensitive detector 118. Depending on the embodiment, a window 108 may be disposed on, or integrated with, the distal end 104a of the rigid imaging tip. In instances where the window 108 is disposed on the distal end, it may either be directly disposed on the distal end of the rigid imaging tip or it may be indirectly disposed on the rigid imaging tip. The window 108 may be transparent to both the excitation wavelengths provided by an associated illumination source as well as wavelengths emitted from a desired imaging agent. However, embodiments in which the window 108 is transparent to other wavelengths as well are also contemplated. While any appropriate shape might be used depending on the particular optics and algorithms used, in one embodiment, the window 108 may have a flat shape to facilitate placing tissue at a desired focal plane when it is pressed against a surgical bed.

In some embodiments, a rigid imaging tip 102 may also include a bend 110 to facilitate access of a medical imaging device into a surgical site. For example, a distal portion 104 of the rigid imaging tip may be angled relative to a proximal portion 106 of the rigid imaging tip. Any appropriate angle between the proximal and distal portions to facilitate access to a desired surgical site might be used. However in one embodiment, an angle α between the proximal and distal portions may be between about 25° to 65° inclusively. For example, a rigid imaging tip may have an angle α that is equal to about 45°. In embodiments including an angled distal portion, the rigid imaging tip 102 may also include a light bending element 122 adapted to bend an optical path 140 through the bent rigid imaging tip. Appropriate light bending elements include, but are not limited to, mirrors and prisms. It should be understood that the specific shapes and dimensions of the rigid imaging tip may be selected to facilitate use in specific surgeries. For example, a medical imaging device may include a distal end 104a with an opening that defines a focal plane with a field of view with a lateral dimension between about 10 mm and 50 mm, though field of views with dimensions both greater than and less than those noted above are also contemplated. This lateral dimension may be a diameter, though geometrical shapes other than a circle might also be used. The rigid imaging tip may also include a distal portion with a length between about 10 mm and 65 mm. In the embodiment shown, this is the distance from the distal end 104a to the point where the optical path contacts the light bending element 122 as depicted in the figure. Such an embodiment may be of particular use in breast surgeries, though it might also be used for other surgeries such as brain cancer surgeries, ovarian cancer surgeries, and other types of cancer surgeries as well.

In other embodiments, it may be desirable for a surgeon to be able to access abnormal tissue in real-time while imaging is taking place. Such an embodiment may facilitate simultaneous identification and removal of abnormal tissue because the surgeon may both identify abnormal tissue in real-time and access it for excision at the same time. To facilitate such access, a rigid imaging tip may include an open distal end as well as one or more openings located on a side of the rigid imaging tip to provide surgical access to a surgical bed. One specific embodiment is described in more detail below referring to FIGS. 4A-5B.

As depicted in the figures, a rigid imaging tip 102 may include a distal portion 104 and a proximal portion 106 coupled to the medical imaging device. The distal portion 104 may include a distal end 104a with an opening 200 that provides access to an associated surgical bed and is also in optical communication with the photosensitive detector 118. One or more openings 204 may be located on a side of the rigid imaging tip to permit surgical access to the surgical bed while still using the medical imaging device. It should be understood that the openings may be located on any side of the rigid imaging tip such that a surgeon may access the surgical bed through the opening 200 provided at the distal end of the rigid imaging tip. In one specific embodiment, at least one support 202 may distally extend from the proximal portion 106 to the distal portion 104 of the rigid imaging tip. Further, the one or more openings 204 may be defined by the at least one support. For example, as shown in the figures, the distal portion 104, supports 202, and proximal portion 106 may be approximately shaped as a conical frustum where the proximal portion 106 has a smaller diameter than the distal portion of the rigid imaging tip 104. Further, three radially spaced supports 202 may distally extend from the proximal portion to the distal portion to define three openings 204 located between the radially spaced supports. While a specific arrangement in shape of the open rigid imaging tip has been depicted, other embodiments including different arrangements of these components as well as different shapes are also possible. In one embodiment, there is a single support or strut extending from the proximal portion 106 to the distal portion 104 and supporting the distal portion 104.

As described in more detail below, when using an open imaging tip, an associated surgical bed may be exposed to ambient light. In order to compensate for the ambient light, an associated illumination source may be adapted to pulse so that exposures of the photosensitive detector for which the illumination source is on consist of a desired fluorescence signal and an ambient light signal. Correspondingly, exposures of the photosensitive detector for which the illumination source is off consist of an ambient light signal. The illumination source may either be pulsed for every other exposure of the photosensitive detector or it may be pulsed at a different time period as the disclosure is not so limited. The signal corresponding to a fluorescence of a desired imaging agent may then be isolated by subtracting exposures corresponding to ambient light from exposures corresponding to both ambient light and the pulsed illumination source.

As noted above, a distal end of a rigid imaging tip may be used to define a focal plane located at a fixed distance from an associated photosensitive detector. However, in some embodiments, a medical imaging device may include an appropriate focusing element 206 to adjust the focal distance of the medical imaging device, see FIGS. 4A-4C. Thus, a focus of the medical imaging device might be selectively adjusted between a focal plane located at the fixed distance defined by the distal end of the rigid imaging tip and a second focal plane located at a second focal distance beyond the distal end of the rigid imaging tip. This may beneficially provide a field of view that may be adjusted between a smaller field of view for close-up examination where a medical imaging device may be placed in contact with tissue and a larger field of view for examination in a standoff mode where the medical imaging device may be held above the tissue being imaged. This may be beneficial in surgeries such as cervical cancer surgery where a surgical site might be on the order of about 20 cm across and it is desirable to detect abnormal tissue over both small and large length scales.

Figure 6:
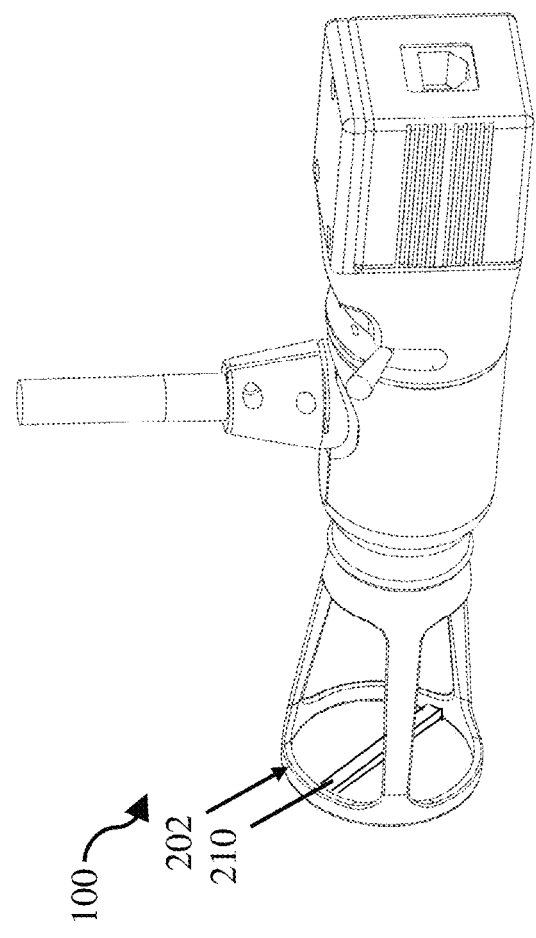
FIG. 6 is a schematic rear perspective view of a rigid imaging tip including a restraining element.

Without wishing to be bound by theory, in embodiments where a field of view defined by an open rigid imaging tip is relatively large, tissue from a surgical bed may protrude past a desired focal plane defined by a distal end of the rigid imaging tip. This may result in the tissue being out of focus due to insufficient depth of field. While it may be possible to increase a depth of field of the medical imaging device, in some embodiments, an open rigid imaging tip may include one or more tissue restraining elements. As illustrated in FIG. 6, the tissue restraining element 210 may be embodied by a bar extending across a distal end 104a of the rigid imaging tip. The restraining element might also correspond to a bar that extends across only a portion of the distal end, a circular element located within an interior region of the distal end, or any other feature capable of restraining tissue from protruding into the rigid imaging tip. Depending on the embodiment, the tissue restraining element 210 may be transparent to the excitation wavelength from a light source and a corresponding fluorescence emission wavelength from a desired imaging agent.

Figure 7:
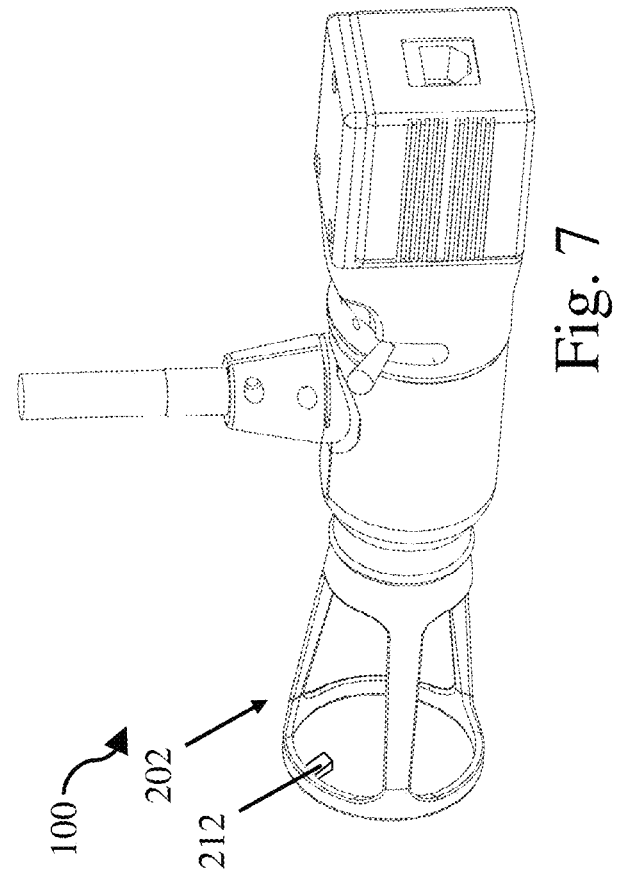
FIG. 7 is a schematic rear perspective view of a rigid imaging tip including an orienting feature.

In other embodiments, a rigid imaging tip may also incorporate an orienting feature 212 to help orient a surgeon relative to a surgical site being imaged by the medical imaging device, see FIG. 7. While any appropriate feature might be used, in one embodiment, the orienting feature 212 may correspond to a tab extending inwards from an interior surface of the rigid imaging tip such that it extends into the field of view of the medical imaging device. Thus, the orienting feature may provide a visual guide within the surgical bed to help guide a surgeon. Additionally, as described in more detail below, the orienting feature 212 may also be used to determine if the medical imaging device is in focus or not. While an orienting feature located within the rigid imaging tip has been depicted in the figures and described above, embodiments in which the orienting feature is located in a position that is not visible to a surgeon while still providing an orienting feature in an image displayed by the device is possible. Additionally, embodiments in which software creates an orienting feature within an image output to an appropriate display without the presence of an orienting feature located in the device is also contemplated.

FIG. 8A-8D depict one embodiment of an illumination source 300. The illumination source may include an LED 302 optically coupled to a light input 120 adapted for outputting light to an associated medical imaging device. As noted previously, the light input 120 may correspond to a fiber-optic guide adapted for coupling to the associated medical imaging device. The LED 302 may be disposed on top of a heat sink 304 and one or more cooling elements 306, such as one or more fans, may be used to remove heat from the illumination source. The LED may also be associated with an appropriate temperature sensor 308 adapted to sense a temperature of the LED for use by an associated controller. As noted above, the LED 302 in one embodiment corresponds to a 50 W LED capable of providing 5.6 W of light with a wavelength of about 630 nm. Such an illumination source may be of particular benefit where a medical imaging device is comparing a fluorescence threshold of healthy tissue to a fluorescence threshold of abnormal tissue due to the relatively high illumination intensity. However, embodiments in which a lower, or higher, intensity illumination source may be used are also contemplated. For example, embodiments in which there is less tissue variability between patients for a particular type of surgery and an absolute abnormal tissue threshold has been determined, a lower intensity illumination source might be used. Additionally, an illumination source may provide any desired wavelength, or spectrum of wavelengths, as the disclosure is not so limited.

Having generally described the various embodiments of a medical imaging device, various methods of use are described in more detail below.

Figure 9A:
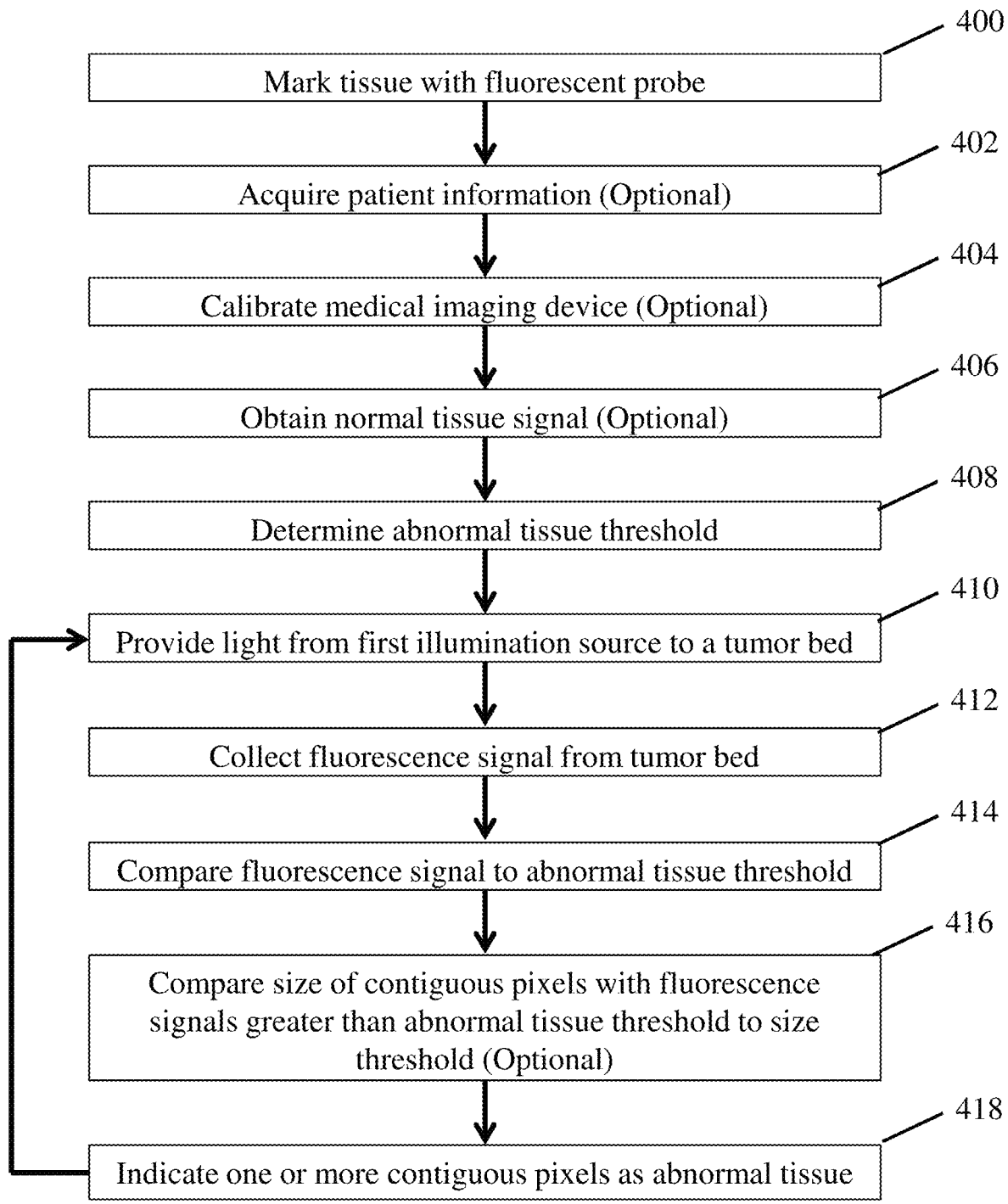
FIG. 9A is a flow diagram of one embodiment of a method for operating a medical imaging device.

FIG. 9A depicts one possible way in which a medical imaging device might be used. As indicated in the figure, tissue may be marked with an appropriate imaging agent at 400. The imaging agent may be provided in any appropriate fashion including, for example, injection and/or topical application. A medical imaging device may optionally prompt a user to input patient information at 402. The patient information might include information such as a name, patient identification number, type of surgical procedure being performed, type of imaging agent being used, and other appropriate information. In some instances, a medical imaging device controller may incorporate warnings when required data fields are not completed. However, user overrides might be used to proceed with imaging in instances where patient information is either unavailable or confidential.

In some embodiments, it may be desirable to calibrate a medical imaging device prior to usage as indicated at 404. This may be done prior to every usage, or it may only be done occasionally as needed to confirm calibration as the disclosure is not so limited. While any appropriate calibration method might be used, in one embodiment, calibration of a medical imaging device might include prompting a user to test a signal brightness generated by a medical imaging device by imaging a fluorescence standard and comparing the average value of that image to a default standard value. Appropriate fluorescent standards may include acrylonitrile butadiene styrene (ABS), though other fluorescent standards might also be used. A medical imaging device control may also prompt a user to determine the system dark noise by imaging a dark standard and/or covering the medical imaging device with a cover. The average pixel value may then be compared to a default value. The controller may then correct for both the dark noise and background variations in real time. The controller may also perform a smoothing operation on an image of the fluorescent standard and may subsequently use that image to correct images during real-time capture. A specific correction method is described in more detail below in the examples.

In some embodiments, the controller may only display pixels within a predefined field of view of the medical imaging device. Pixels located outside of the field of view may be assigned a preset value including, for example, a value of zero. Pixels located outside of the field of view may be determined by a signal cutoff value based on the fluorescent standard image noted above. Pixels that fall below the cut off value may be determined as being outside of the field of view.

As part of calibrating a medical imaging device, in some embodiments it may be desirable to confirm a focus and resolution of the medical imaging device prior to use. In such an embodiment, a controller of the medical imaging device may identify the location of a constant feature, such as an orienting feature protruding into the field of view and/or an edge of the field of view of the medical imaging device for evaluating the focus. A standard signal corresponding to the feature and/or edge of the field of view may be stored within a controller of the medical imaging device. The standard signal may have a characteristic length over which a signal corresponding to the of the field of view and/or the constant feature transitions when in focus. Consequently, when imaging a standard as noted above, the controller may compare a transition length associated with an edge of the field of view and/or the constant feature to the previously determined characteristic length. If the imaged transition length is different from the characteristic length, a user may adjust the focus manually. Alternatively, in some embodiments, the controller of the medical imaging device may automatically adjust the focus. While focusing may confirmed and adjusted during calibration, in some embodiments, focus may be adjusted during imaging of a surgical bed as well.

It should be understood that the various corrections noted above may either be performed individually or in combination.

After calibrating the medical imaging device, in some embodiments, a controller may prompt a user to determine a normal tissue signal at 406. A normal tissue signal may be determined by having a user place a rigid imaging tip of the device at a known portion of healthy tissue and collecting an image. A fluorescent signal corresponding to the normal tissue may then be captured by the medical imaging device to establish the normal tissue signal for subsequent usage. While a single normal tissue signal obtained from a single image might be used, in some embodiments, a controller may determine an average normal tissue signal using an average of several images of normal tissue.

The medical imaging device may also determine an abnormal tissue threshold at 408. In some embodiments, an abnormal tissue threshold may be determined by setting a value that is a predetermined amount greater than the normal tissue signal. However, in other embodiments, the abnormal tissue threshold may simply correspond to a known absolute threshold corresponding to a particular imaging agent and tissue being imaged. For example, an abnormal tissue threshold for breast cancer using LUM015 may be greater than about $16.6 \times 10^{10}$ counts/s/cm$^2$. This abnormal threshold was determined using a normal tissue signal of about $11.2 \times 10^{10}$ counts/s/cm$^2$ with a standard deviation of about $1.8 \times 10^{10}$ counts/s/cm$^2$. A corresponding mean abnormal tissue threshold was also determined to be about $55.7 \times 10^{10}$ counts/s/cm$^2$. Therefore, the abnormal tissue threshold is about three standard deviations higher than the normal tissue signal while still being greatly less than the identified abnormal tissue threshold. While a particular threshold has been indicated above for a particular surgery, the abnormal tissue threshold limit could be any appropriate value for a given imaging agent and tissue being imaged.

In instances where a user notices that a medical imaging device is not completely identifying regions of abnormal tissue, it may be desirable to adjust the abnormal tissue threshold to appropriately identify the abnormal tissue. In such an embodiment, determining an abnormal tissue threshold may also include permitting a user to adjust the abnormal tissue threshold using a numerical input, slider provided on a graphical user interface, or other appropriate input. In order to prevent false negatives, it may be desirable to only permit lowering of the abnormal tissue threshold. Without wishing to be bound by theory, this would increase the chance of false positives while limiting the chance of false negatives.

After appropriately setting up a medical imaging device and measuring a normal tissue signal and/or abnormal tissue threshold, a medical imaging device may then be used to image a surgical bed or other tissue section. As indicated at 410, the medical imaging device may provide light from a first illumination source to an associated surgical bed. The light provided by a first illumination source may include an excitation wavelength of an imaging agent used to mark the tissue as noted above. The medical imaging device may then collect a fluorescence signal emitted from the imaging agent located in the tumor using an appropriate photosensitive detector at 412. In some embodiments, collecting the fluorescence signal from the surgical bed may also include collecting an autofluorescence signal from tissue located within the surgical bed. The collected fluorescence signal may be compared to the abnormal tissue threshold at 414. Pixels of the photosensitive detector with fluorescence signals that are greater than the abnormal tissue threshold may be identified as corresponding to abnormal tissue. In some embodiments, a size of one or more contiguous pixels with fluorescence signals that are greater than abnormal tissue threshold may optionally be compared to a size threshold at 416 such that sizes greater than the size threshold may be identify as abnormal and sizes less than the size threshold may be disregarded. This size threshold may correspond to sizes that are less than a corresponding cell size. However, size thresholds that are larger than a corresponding cell size are possible. For example, the size threshold may be between about 5 µm and 160 µm, 5 µm and 30 µm, 5 µm and 50 µm, or any other appropriate size. Size thresholds both greater than and less than the ranges noted above are also contemplated.

After identifying one or more areas within a field of view corresponding to abnormal tissue, a controller of a medical imaging device may both output an image to an appropriate viewing device and indicate areas corresponding to abnormal tissue at 418. For example, the controller might output an image to a viewing screen and it may indicate locations of abnormal tissue depicted on the screen by highlighting or using a geometric shape. In one specific embodiment, the controller may highlight abnormal tissue corresponding to a size that is greater than about 2 mm$^2$ and may use a geometric shapes such as an arrow, a circle, a square, a rectangle, a non-symmetric closed loop, or other appropriate shape to indicate abnormal tissue corresponding to a size that is less than about 2 mm$^2$ that would be difficult for a surgeon to visually identify. It should be understood that different sizes for indicating areas of abnormal tissue either greater than or less than 2 mm$^2$ are also possible.

It should be understood that a medical imaging device operated in the above-noted matter may continuously provide excitation light to a surgical bed, collect the resulting fluorescence signals, identify areas of abnormal tissue and indicate the location of those identified areas of abnormal tissue to a user. Therefore, a surgeon may be able to view real-time images indicating the presence, or lack thereof, of abnormal tissue within a surgical bed without the need for lengthy testing of excised tissue samples. In some embodiments, the controller of the medical imaging device may also provide for either video and/or picture capture to aid in performing and/or documenting a surgical procedure.

Figure 9B:
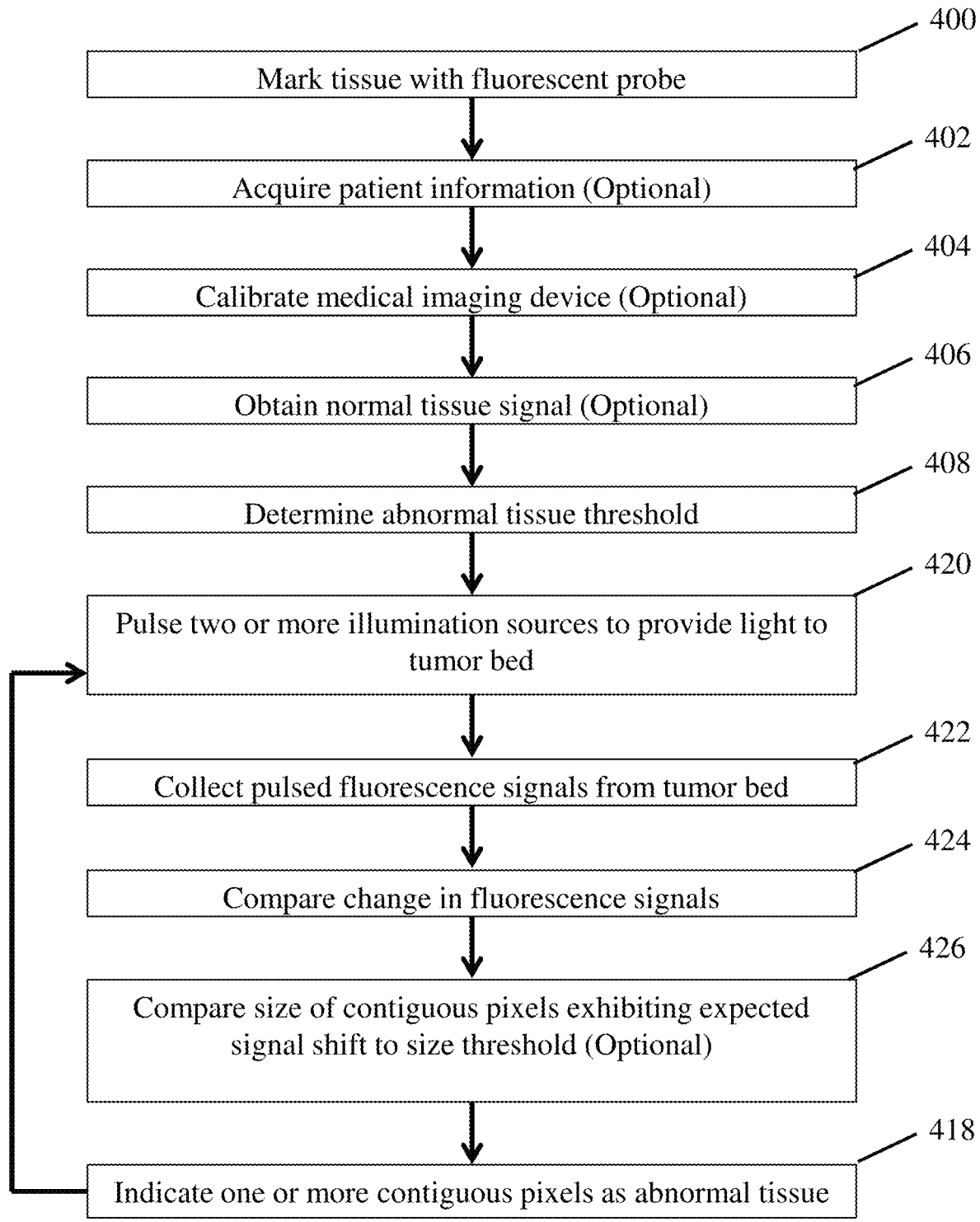
FIG. 9B is a flow diagram of one embodiment of a method for operating a medical imaging device.
Figure 9C:
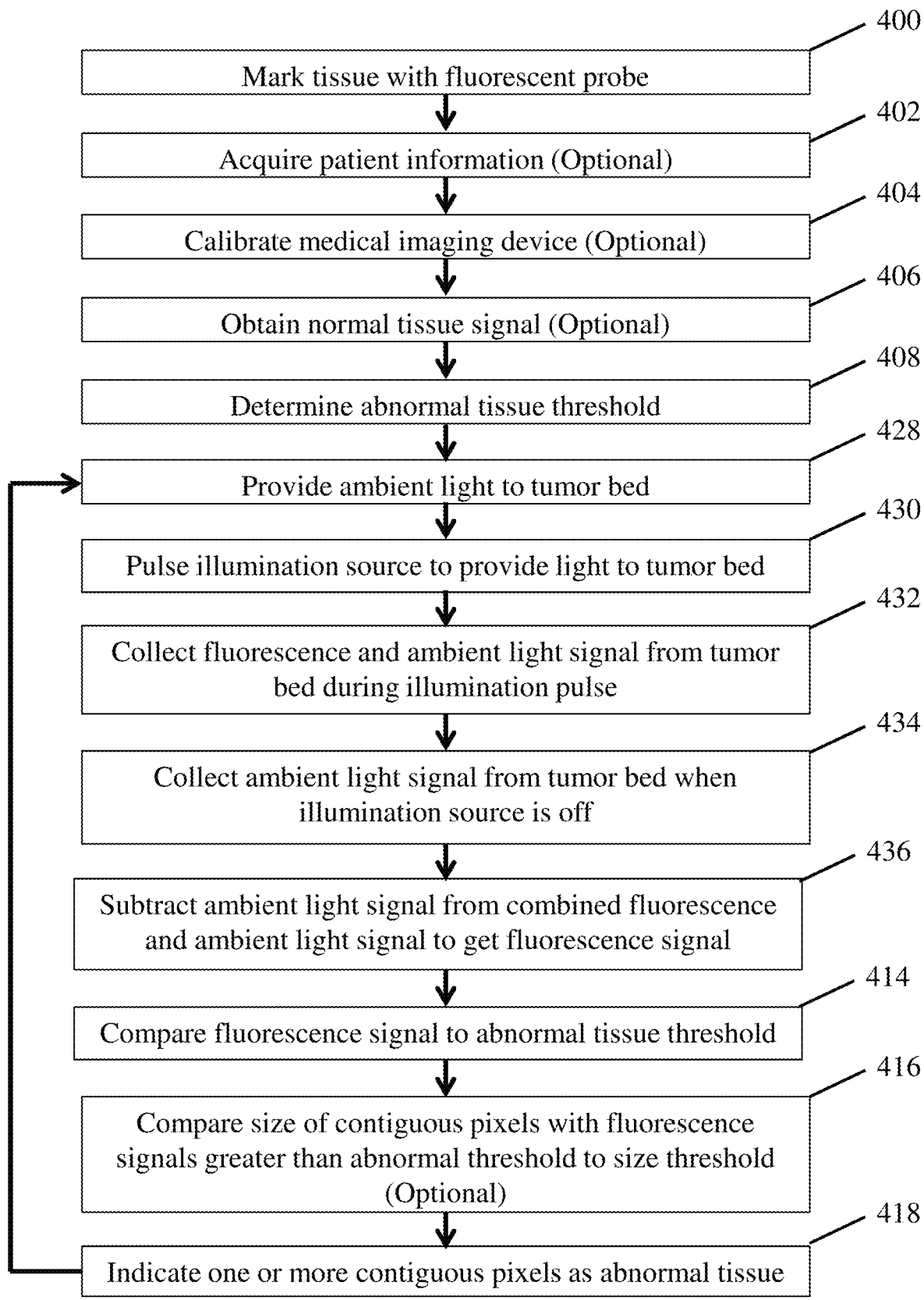
FIG. 9C is a flow diagram of one embodiment of a method for operating a medical imaging device.

FIGS. 9B and 9C depict two other methods for operating a medical imaging device. Similar to the above, these methods may include marking tissue with a first imaging agent. Additionally, as above, a medical imaging device may optionally acquire patient information, calibrate the medical imaging device, and optionally obtain a normal tissue signal as well as an abnormal tissue threshold. The medical imaging device may then identify areas of abnormal tissue as described in more detail below prior to indicating one or more contiguous pixels as corresponding to abnormal tissue.

FIG. 9B depicts a method for mitigating a large autofluorescence signal from adjacent normal tissue. However, such a method might also be used in instances where a large autofluorescence signal is not present as the disclosure is not so limited. In the depicted method, two or more illumination sources may be alternatingly pulsed to provide light to a surgical bed at 420. The two or more illumination sources may provide light including two or more different excitation wavelengths of an associated imaging agent. For example, a first illumination source may provide a first excitation wavelength and a second illumination source may provide a second excitation wavelength. In embodiments where a light directing element, such as a dichroic mirror, is used, the excitation wavelengths may be less than a wavelength cutoff of the light directing element. In some embodiments, additional illumination sources, such as a third illumination source, may be used to provide additional excitation wavelengths. Regardless of the particular number of illumination sources used, the two or more illumination sources may correspond to any appropriate structure. For example, two different color LEDs, lasers, or spectrally filtered lamps might be used. Additionally, the illumination sources might be integrated into a single system, such as a single lightbox, or they may be integrated into separate systems. The pulsing of the two or more illumination sources may be controlled such that they are triggered for every other exposure of an associated photosensitive detector though other timings for the pulses are also contemplated.

An associated photosensitive detector may collect the fluorescence signals emitted from the surgical bed corresponding to the separate illumination sources at 422. A controller of the medical imaging device may then compare a fluorescence signal intensity and/or wavelength shift in the detected signal of each pixel between the separate exposures. This signal shift may then be correlated to the expected shift from the first excitation wavelength to the second excitation wavelength for the associated imaging agent. Pixels exhibiting the expected signal shift may then be identified as correlating to abnormal tissue. Correspondingly, pixels that do not exhibit the expected signal shift may be identified as correlating to normal tissue. Similar to the above, the controller may optionally compare a size of one or more contiguous pixels exhibiting the expected signal shift to a size threshold to also determine if the identified pixels correspond to abnormal tissue.

FIG. 9C depicts a method for mitigating interference from ambient light being reflected from within a surgical site being imaged. Such a method may be used with any medical imaging device, but in one embodiment, a medical imaging device including an open rigid imaging tip may employ such a method. As indicated in the figure, ambient light may be provided to a surgical bed at 428. The ambient light may either be incident upon the surgical bed because a medical imaging device is being operated in a standoff mode and/or because an imaging tip of the device includes openings for surgical access through which the light enters. An illumination source adapted to provide an excitation wavelength of the imaging agent may be pulsed to deliver light to the surgical bed at 430. While the illumination source may be pulsed in any appropriate, in one embodiment, the illumination source may be pulsed every other exposure of an associated photosensitive detector. The photosensitive detector may then collect a combined fluorescence and ambient light signal emitted from the surgical bed during one exposure at 432. Separately, the photosensitive detector may collect an ambient light signal emitted from the surgical bed during another exposure at 434 when the illumination source is off. A controller of the medical imaging device may then subtract the ambient light signal from the combined fluorescence and ambient light signal to produce a fluorescence signal at 436. The fluorescence signal for each pixel of the photosensitive detector may then be compared to an abnormal tissue threshold and optionally a size threshold to identify the presence of abnormal tissue as previously noted.

Figure 19:
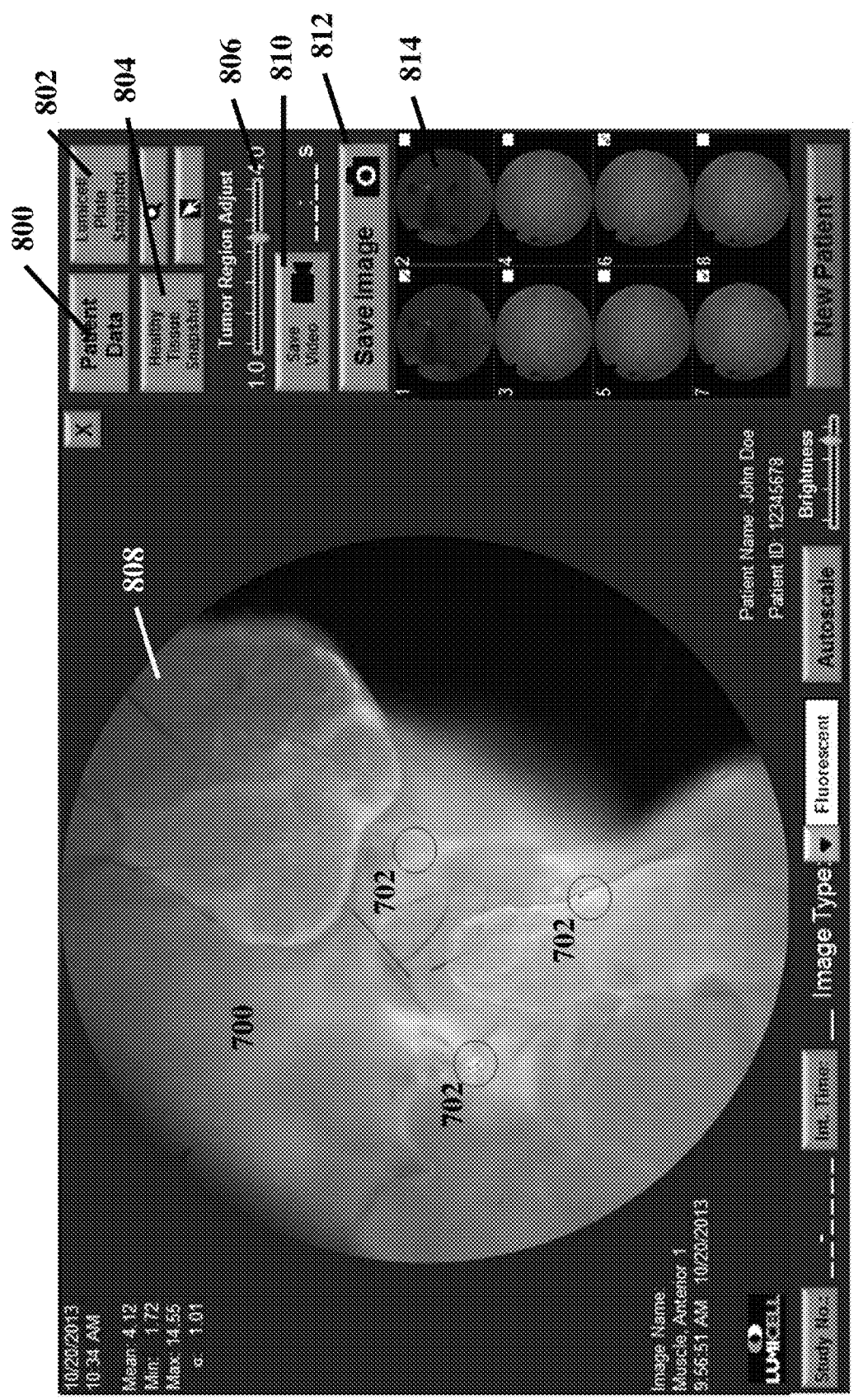
FIG. 19 is an exemplary screenshot of an interface that might be used to present images highlighting regions containing abnormal tissue within a surgical bed.

FIG. 19 depicts one embodiment of a graphical user interface used for indicating the location of abnormal tissue 702 relative to normal tissue 700. As shown in the figure, in addition to showing a real time image 808 indicating the location of abnormal tissue as described above, the graphical user interface may include buttons for initiating procedures such as patient data acquisition 800, calibrating the system against a fluorescent standard 802, calibrating a normal tissue signal 804, and adjustment of an abnormal tissue threshold 806. The interface may also include buttons for saving videos 810 and images 812. One or more smaller screen shots 814 from the saved videos and images may also be displayed on a screen to aid a surgeon in keeping track of multiple locations within a surgical bed, the progress of a surgery over time, or other appropriate use. It should be understood that other arrangements might also be used.

Having generally described a medical imaging device and its methods of use above, several non-limiting examples of its application and implementation are provided below.

Example

Autofluorescence Mitigation

Figure 10A:
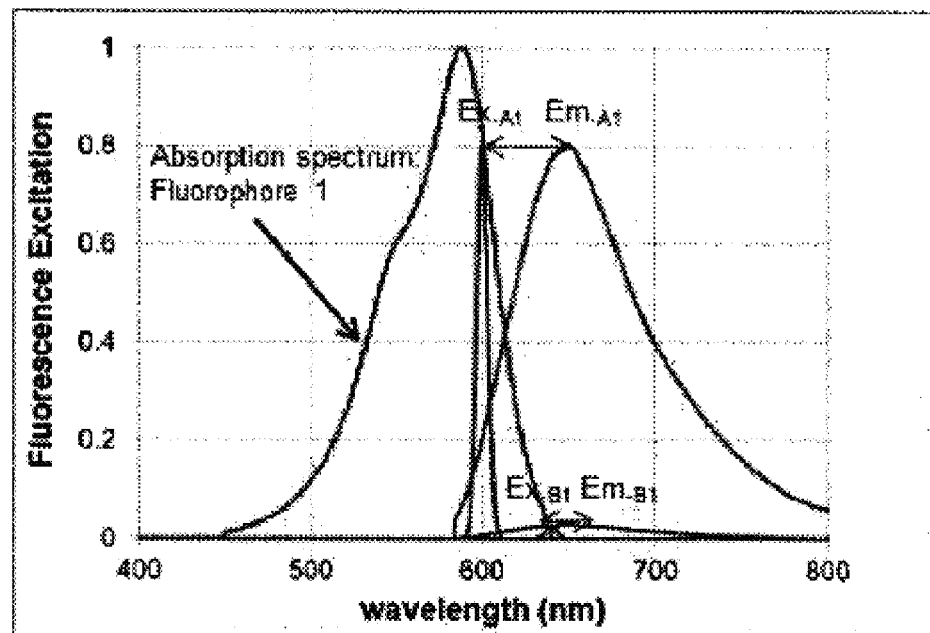
FIG. 10A is a graph of fluorescence intensity of a fluorphore for different excitation wavelengths.
Figure 10B:
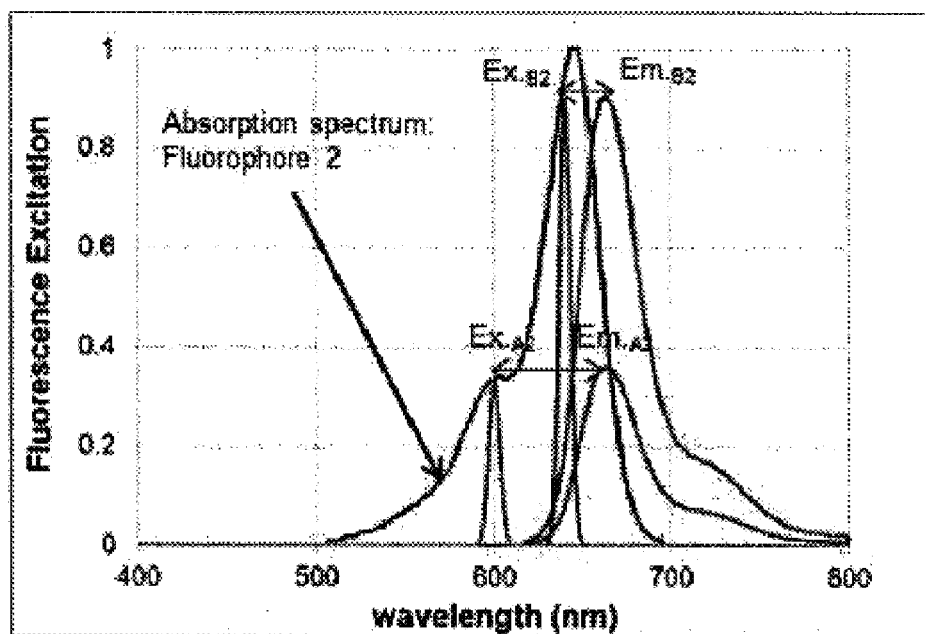
FIG. 10B is a graph of fluorescence intensity of a fluorphore for different excitation wavelengths.

FIGS. 10A and 10B present graphs of emission intensities for two separate fluorphores, mPlum and cy5, exposed to different excitation wavelengths. As shown in FIG. 10A the shift in excitation wavelength yielded a decrease in emission intensity of about 96% for fluorphore 1 which was mPlum. Additionally, a shift in excitation wavelength yielded an increase in emission intensity of about 156% for fluorphore 2 which was cy5. As noted above, this shift in emission intensity in response to different excitation wavelengths can be used to identify a particular fluorphore surrounded by autofluorescing tissue that exhibits a different shift in emission intensity and/or wavelength in response to the same excitation wavelengths.

Example

Correcting for Ambient Light

Figure 11A:
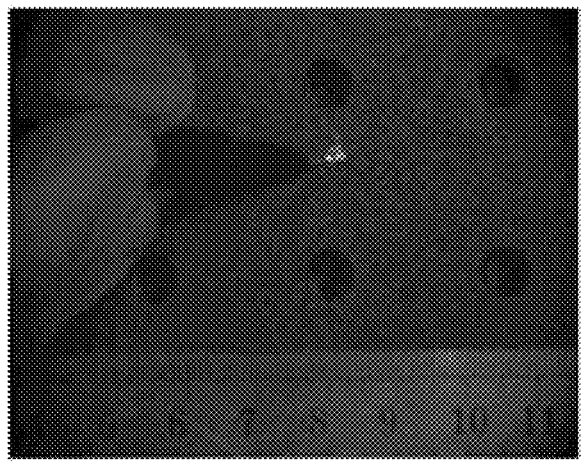
FIG. 11A is an image taken with room light and a fluorescence signal.
Figure 11B:
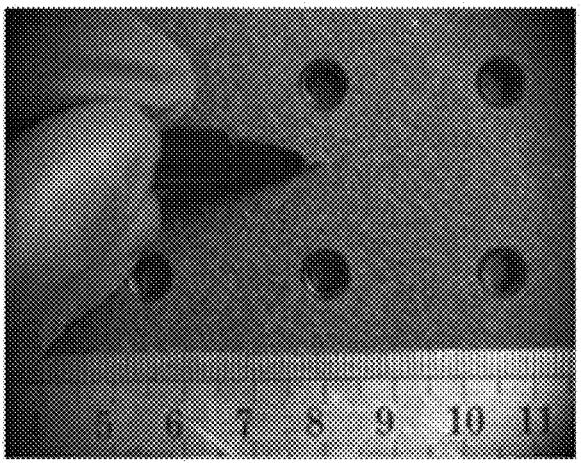
FIG. 11B is an image taken with room light.
Figure 11C:
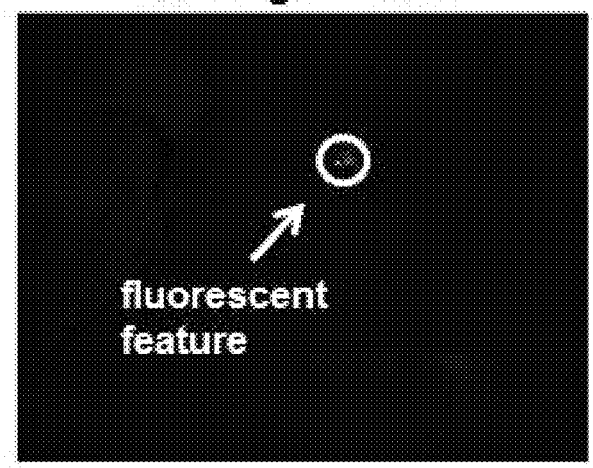
FIG. 11C is an image generated by subtracting the imaging taken with room light from the image taken with room light and a fluorescence signal.

FIG. 11A-11C illustrate a method for identifying a fluorescence signal in the presence of ambient light. In FIG. 11A a surface including a fluorescent material is subjected to both ambient light and an excitation wavelength generating an ambient light signal and fluorescence signal. Subsequently, the surface is exposed to just ambient light as illustrated in FIG. 11B. The image captured in FIG. 11B corresponding to just an ambient light signal may then be subtracted from FIG. 11A corresponding to an ambient light and fluorescence signal. The resulting image is presented in FIG. 11C where the bright feature indicated in the figure corresponds to the fluorescence signal.

Example

Medical Imaging Device Characteristics

Exemplary characteristics form medical imaging devices used during initial studies are provided below in Table I. The provided characteristics include image side f-number, object side f-number, illumination flux, excitation wavelength, emission wavelength, objective lens focal length, and imaging lens focal length. It should be understood that different values of these physical characteristics than those presented below might also be used.

TABLE I

| Device | Image side f/# unitless | Object side f/# Unitless | Illum. Flux mW/cm² | Excitation Wavelength nm | Emission wavelength nm | Objective lens focal length mm | Imaging lens focal length mm |
|---|---|---|---|---|---|---|---|
| 1 | 3.3 | 4.17 | 172 | 628-672 | 685-735 | 50 | 40 |
| 2 | 3.0 | 13.3 | 64 | 590-650 | 663-738 | 200 | 25 |

Example

Standard Calibration

Figure 12A:
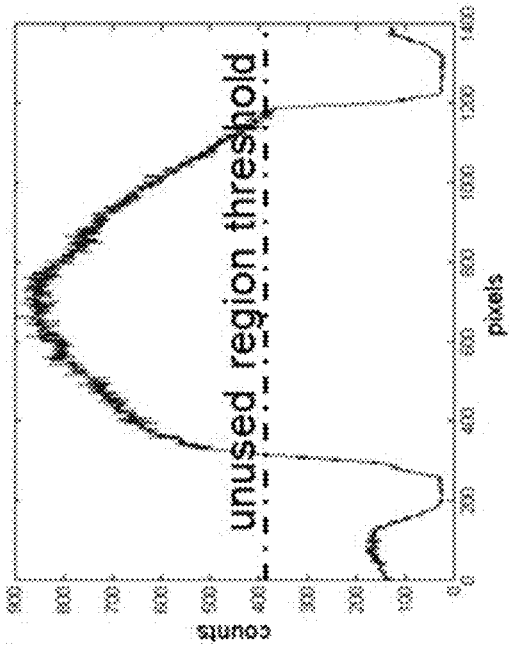
FIG. 12A is an image captured with an imaging device showing a desired field of view and portions outside the field of view.
Figure 12B:
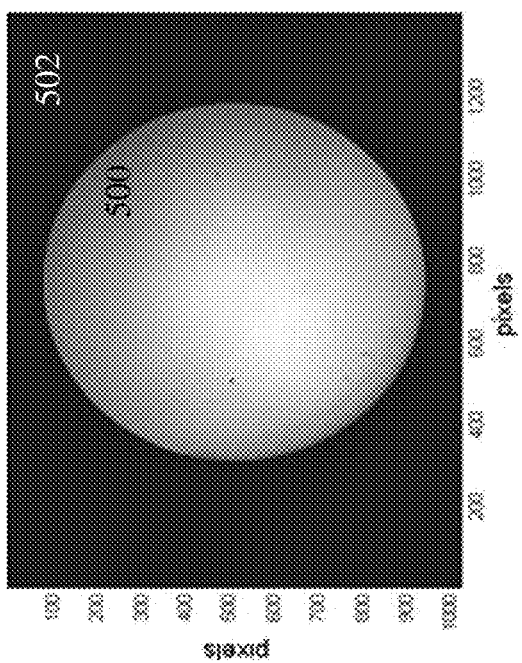
FIG. 12B is a graph depicting the photon counts for pixels within the field of view and outside the field of view.
Figure 12C:
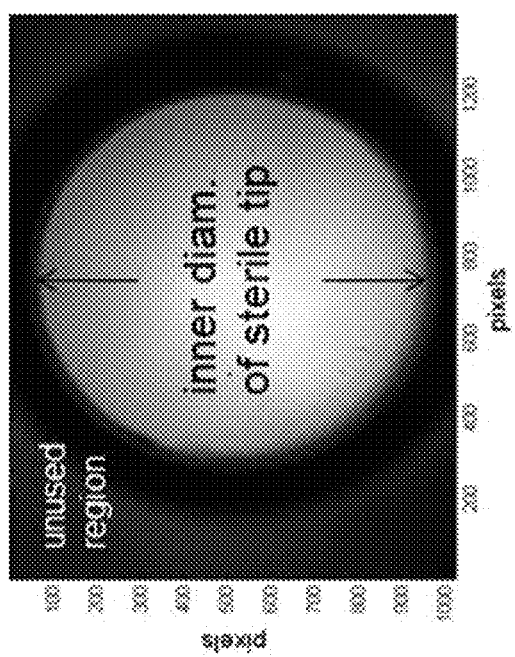
FIG. 12C is an image with the pixels outside the field of view set to a desired value.

FIG. 12A-12C depict the imaging and analysis of a acrylonitrile butadiene styrene (ABS) fluorescent standard imaged with a medical imaging device. Alternatively, the standard might correspond to a quantum dot (QD) plate or other appropriate material. The fluorescence signals from an ABS fluorescent standard and a QD plate standard as measured with the devices 1 and 2 described above are shown in Table II below. Due to the particular construction of the device, the measured signals are reported in counts/s/cm².

TABLE II

| Device | QD Plate ($10^{10}$ counts/s/cm²) | ABS ($10^{10}$ counts/s/cm²) |
|---|---|---|
| 1 | 5.8 | 7.4 |
| 2 | 35 | 8.8 |

FIG. 12A is a raw image of an ABS standard. FIG. 12B presents the counts per pixel across a width of the image. As illustrated in the figure, pixels corresponding to the field of view 500 have a count value that is greater than a threshold number of counts per exposure. Pixels that have a number of counts that is less than the threshold number of counts per exposure can this be determined to be outside the field of view. A controller and medical imaging device may then set a value of the pixels 502 outside of the field of view to a preset value such as zero as illustrated in FIG. 12C.

In addition to using an image of the fluorescent standard to determine the field of view, a dark noise image may be taken for additional calibration purposes. Values associated with the dark noise image are dependent upon the exposure length. Therefore, the exposure length of the dark field image may be correlated with the exposure length expected during use of a medical imaging device. Without wishing to be bound by theory, the dark noise associated with each individual pixel includes both a time dependent and time independent component. Depending on the particular embodiment, the dark noise value associated with each pixel may be determined by capturing a dark noise image with a proper exposure length. Alternatively, the time independent component may be added to the time dependent component of the dark noise value integrated over the desired exposure time.

As noted above, images captured by a medical imaging device may be corrected using the dark noise and fluorescent standard images. More specifically, the fluorescence standard image ($I_{FS}$) may be smoothed using a simple, running-window average, and then normalized by the maximum fluorescence signal within the standard image [max($I_{FS}$)]. The dark noise image ($I_{DN}$) may then be subtracted from the real-time image ($I_{RT}$) being captured by the medical imaging device during use. The normalized fluorescence standard image may then be divided out of the "dark noise" corrected image to produce the output image ($I_{out}$). A representative formula is provided below. However, it should be understood that other methods of calibrating a medical imaging device and correcting an image are also possible.

$$I_{out} = \frac{I_{RT} - I_{DN}}{I_{FS}/\max(I_{FS})}$$

Example

Focus

Figure 13A:
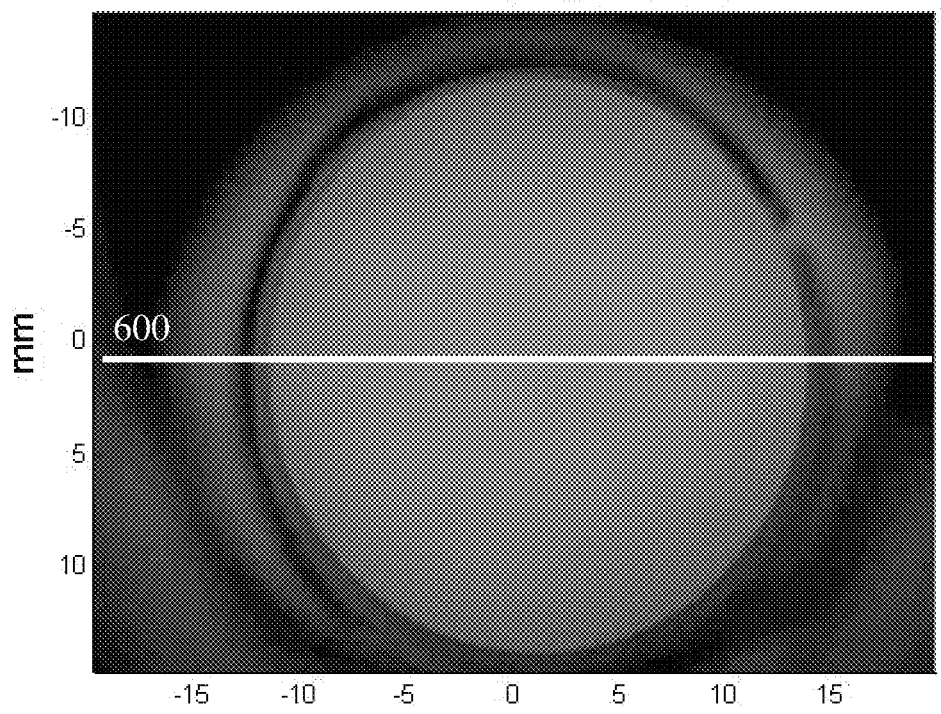
FIG. 13A is an image of a fluoroscopic standard while in focus.
Figure 13B:
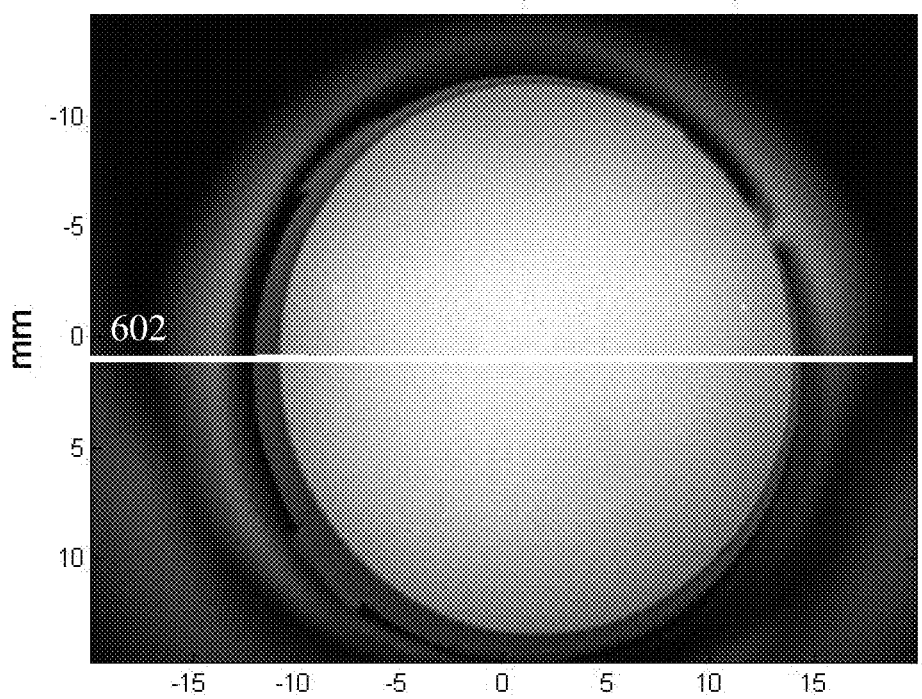
FIG. 13B is an image of a fluoroscopic standard while out of focus.
Figure 14A:
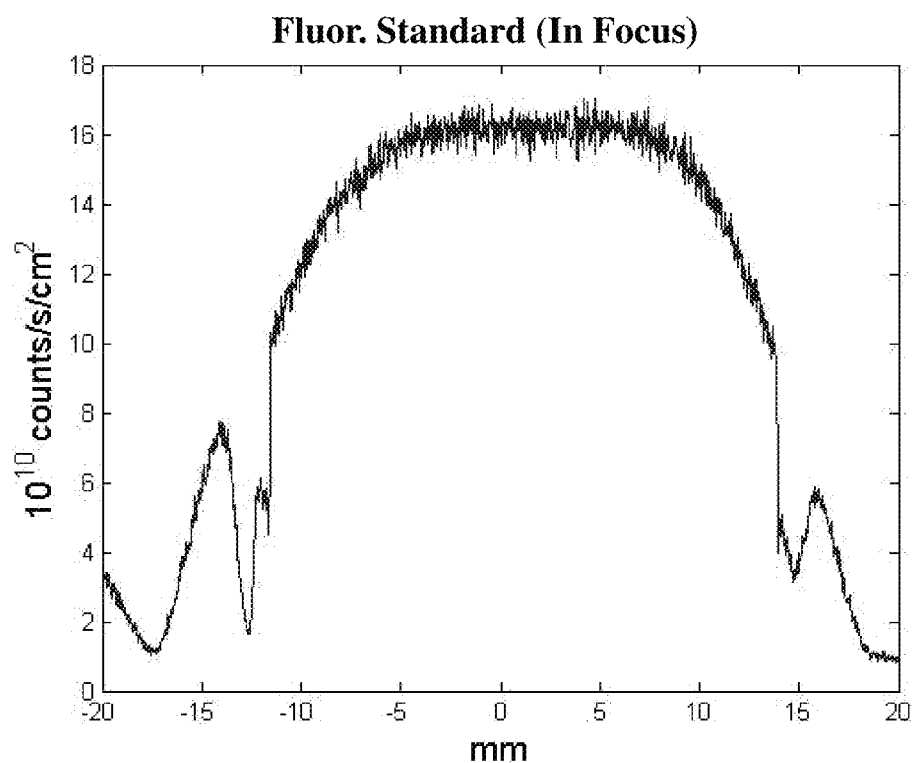
FIG. 14A is a graph of photon counts for a line taken across FIG. 13A corresponding to an in focus image.
Figure 14B:
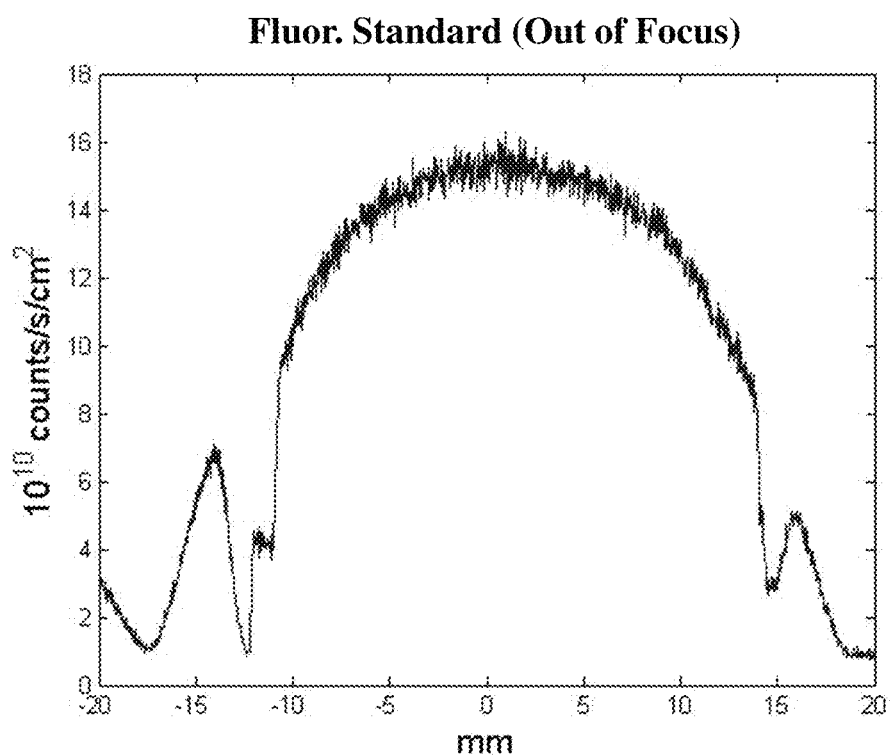
FIG. 14B is a graph of photon counts for a line taken across FIG. 13B corresponding to an out of focus image.
Figure 15A:
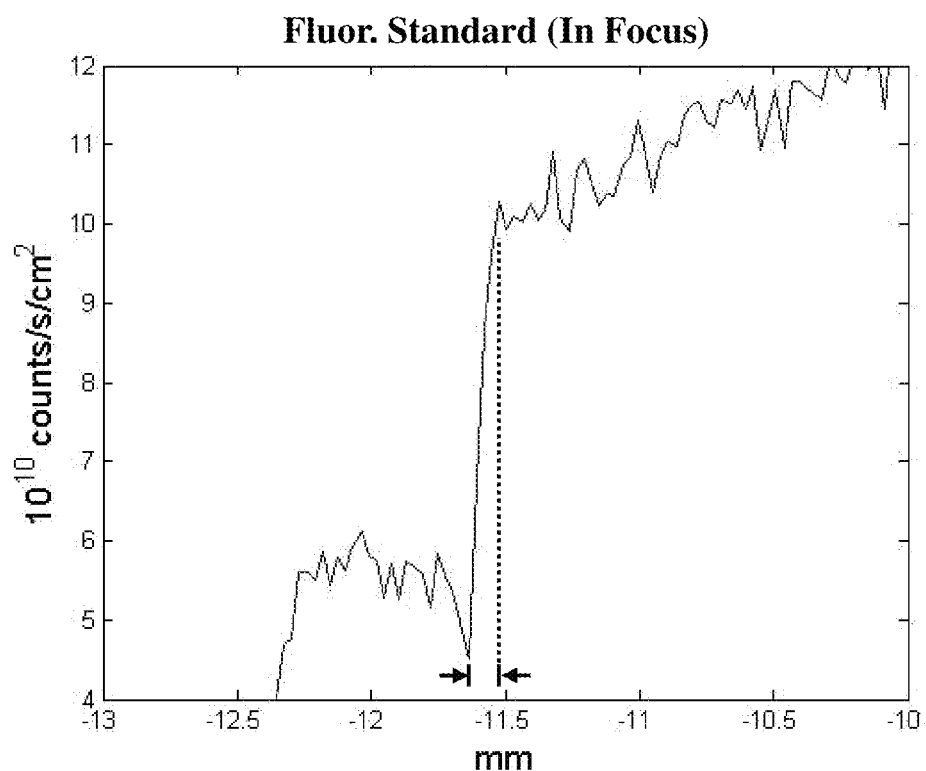
FIG. 15A is a close-up of a portion of the graph presented in FIG. 14A corresponding to an in focus image.
Figure 15B:
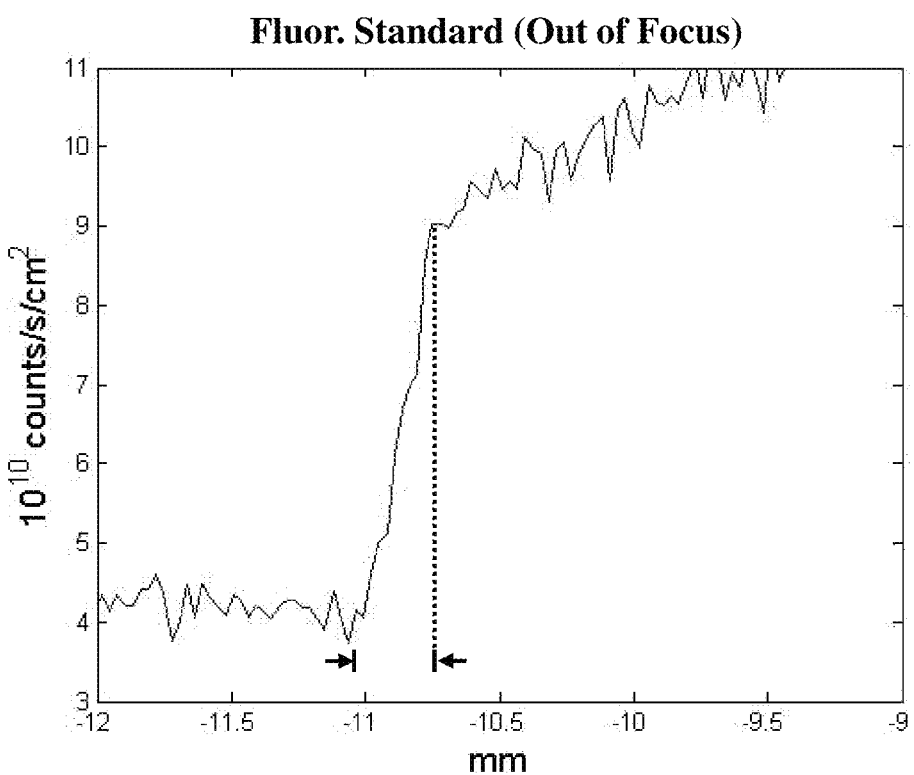
FIG. 15B is a close-up of a portion of the graph presented in FIG. 14B corresponding to an out of focus image.

FIG. 13A-15B depict the imaging and analysis of a acrylonitrile butadiene styrene (ABS) fluorescent standard imaged with a medical imaging device while in focus and out of focus. FIG. 13A is a raw image of a fluorescent standard in focus and FIG. 13B is a raw image of a fluorescent standard autofocus. The images were taken with device 2 as described above. Lines 600 and 602 represent the slices along which the signals presented in FIGS. 14A and 14B were taken. FIGS. 14A and 14B depict a standard signal profile across the raw image for both a focused and unfocused image. However, as shown in the zoomed in FIGS. 15A and 15B a transition length between the pixels located at an edge of the field of view and the pixels located outside the field of view changes from between about 80 μm to 160 μm for the in focus image to a transition length that is greater than 310 μm for the presented image. Therefore, the controller of the medical imaging device used a threshold transition length of 160 μm. However, it should be understood that the particular transition length, or range of transition lengths, used for a particular imaging device will depend on the optics and focal distances being used.

Example

Imaging of a Dog with Naturally Occurring Lung Cancer

Figure 16A:
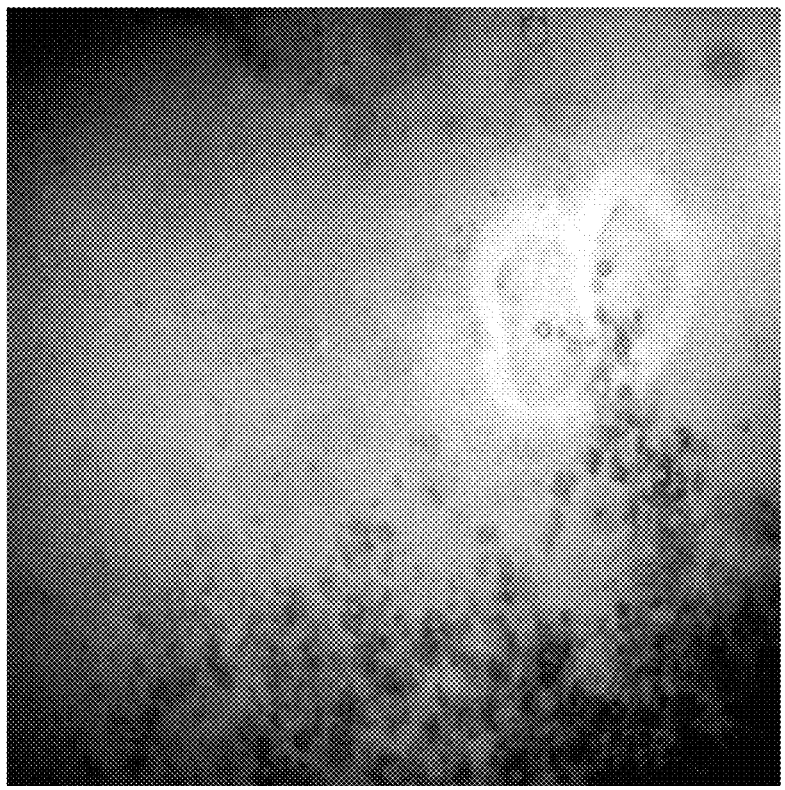
FIG. 16A is an image of a tumor from a dog with naturally occurring lung cancer injected with LUM015.
Figure 16B:
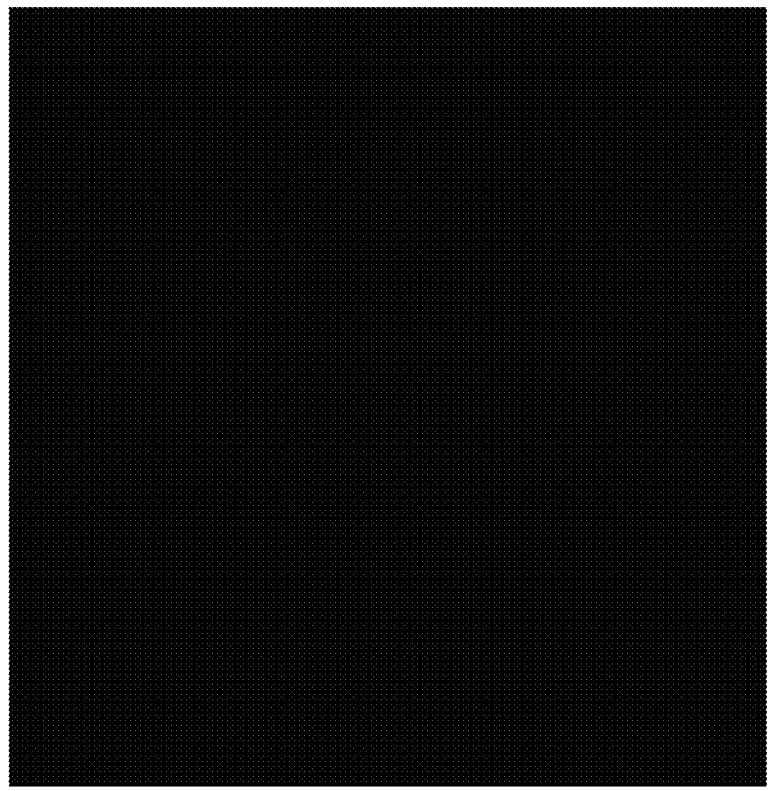
FIG. 16B is an image of normal lung tissue from a dog with naturally occurring lung cancer.

A dog with naturally occurring lung cancer was injected with LUM015 and subsequently imaged intraoperatively using a medical imaging device. The fluorescence image from the tumor is depicted in FIG. 16A. The fluorescence signal corresponding to abnormal tissue present within the tumor is clearly visible. This is contrasted with the image of normal lung tissue depicted in FIG. 16B where virtually no fluorescence signal was observed. The tumor to background ratio determined using these images was about 3 to 1.

Example

Indicating Locations of Abnormal Tissue

Figure 17A:
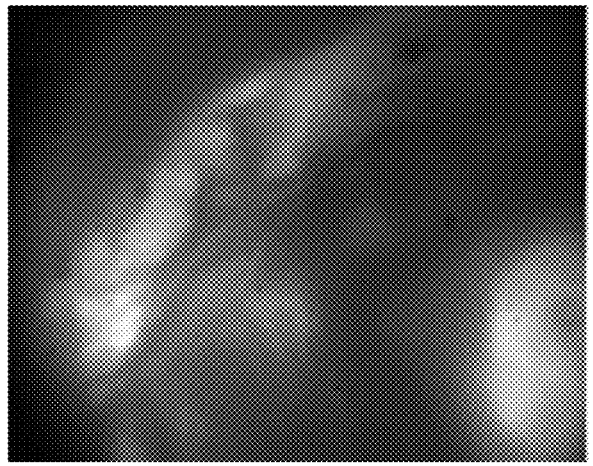
FIG. 17A is a raw image taken using LUM015 of a mouse-sarcoma surgical bed after surgery in a mouse following IV injection of LUM015.
Figure 17B:
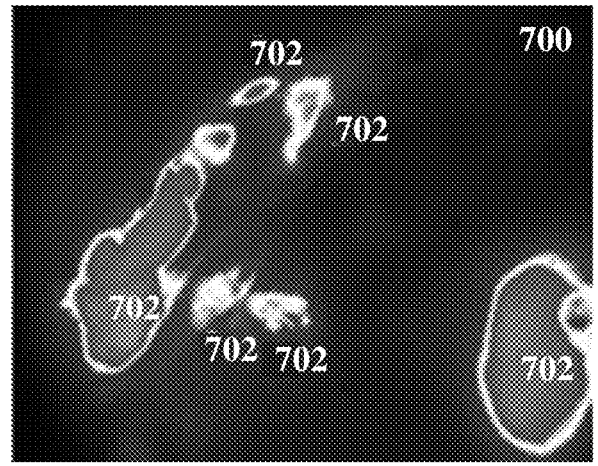
FIG. 17B is the same image as FIG. 17A analyzed by a detection system to highlight regions containing residual cancer.
Figure 17C:
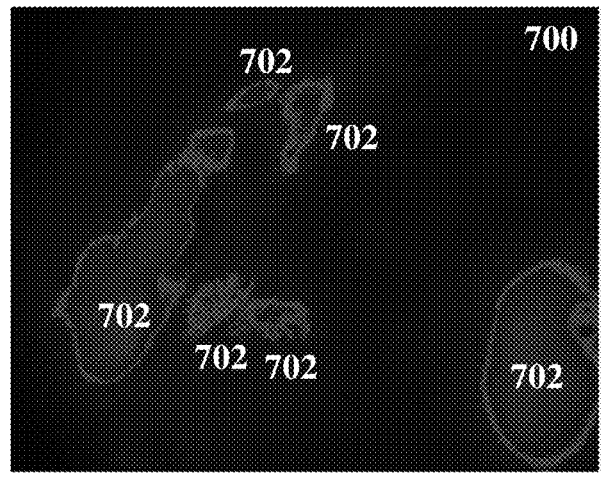
FIG. 17C the same image as FIG. 17A analyzed by a detection system to highlight regions containing residual cancer.
Figures 18A, 18B:
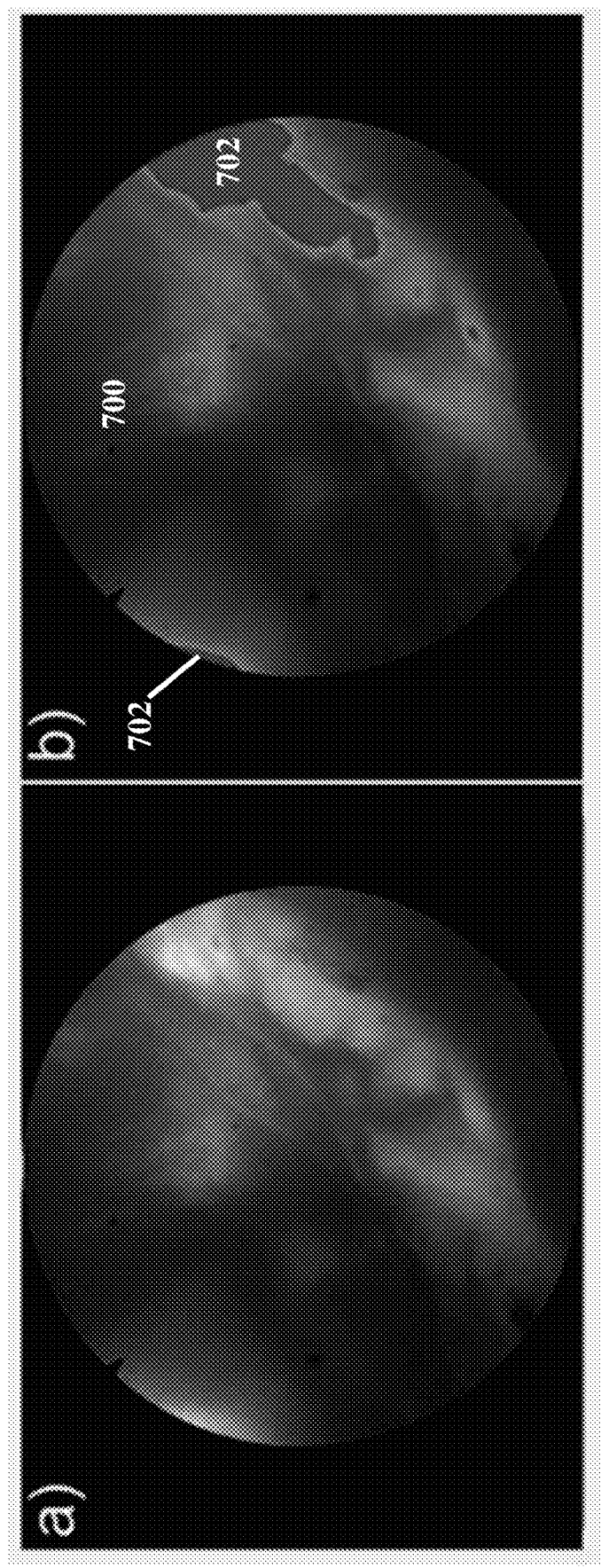
FIG. 18A is a raw image of a surgical bed.
FIG. 18B is the same image as FIG. 18A analyzed by a detection system to highlight regions containing abnormal tissue.

FIGS. 17A and 18A are raw images taken of a mouse-sarcoma surgical bed after surgery in a mouse following IV injection of LUM015. FIGS. 17B, 17C and 18B illustrate several different ways that abnormal tissue 702 may be indicated relative to normal tissue 703. More specifically, FIGS. 17B and 17C illustrate indicating the location of abnormal tissue through the use of appropriate indicating geometry such as non-symmetrical closed loops following a periphery of the abnormal tissue. In contrast, FIG. 18B illustrates indicating the location of abnormal tissue by highlighting that tissue with an appropriately contrasting color such as red, green, purple, yellow, or other desired color. In either case, the presented images may indicate the presence of the abnormal tissue to a surgeon to aid in a surgical procedure.

Example

Comparison of LUM033 and LUM015 in Mice

Table III presents test results performed on mice using different imaging agents to image a soft tissue sarcoma. The resulting ratios of tumor to muscle signal observed were approximately 6.9 for LUM015 and 6.3 for LUM033.

In addition to the above, and without wishing become by theory, cathepsin and MMP measurements in mice are significantly lower in mice tumors than in human tumors and as expected the benefit of the tri-mode protease activated probe was reduced. Therefore, the tumor and muscle signals in LUM015 were about one half that of LUM033 due in part to the lower levels of protease expression in the murine models. Consequently, improved signal generation associated with LUM015 is expected in humans.

TABLE III

| Imaging agent | Dose (mouse) | Tumor Signal $\times 10^{10}$ | Muscle Signal $\times 10^{10}$ | Ratio of Tumor to Muscle Signal |
|---|---|---|---|---|
| LUM015 | 3.5 mg/kg | 36 ± 15 (n = 15) | 5.2 ± 1.9 | 6.9 |
| LUM033 | 3.5 | 63 ± 18 (n = 11) | 10 ± 3.4 | 6.3 |

Example

Performance in Mice, Dogs, and Humans Across Cancer Types

Table IV presents sensitivity, specificity, and tumor to normal tissue signal ratios for several types of tissues in mice, dogs, and humans. As illustrated by the data below, the medical imaging devices described herein coupled with appropriate imaging agents are able to obtain superb sensitivity and specificity across these species and several cancer types.

TABLE IV

| Species and cancer type | Endpoint | Sensitivity and Specificity | Tumor-to-normal tissue signal ratio |
|---|---|---|---|
| Humans (n = 25) | Pathology of resected tissue | 89%, 88% | 5:1 |
| Dogs with lung, mammary gland, sarcoma, mast cell tumors (n = 12) | Pathology of resected tissue and negative margins | 93%, 91% | 7:1 |
| Mice with sarcoma (n = 18) | Pathology of resected tissue | 90%, 80% | 8:1 |
| Mice with sarcoma (n = 34) | Local recurrence | 80%, 80% | 8:1 |
| Mice with breast cancer (n = 44) | Pathology of resected tissue | 100%, 100% | 8:1 |

Example

Initial Human Trials

Nine patients (8 sarcoma patients and 1 breast cancer patient) were injected intravenously with LUM015 (3 with 0.5 mg/kg and 6 with 1 mg/kg) and then underwent standard surgery and the resected tissue was imaged at a pathology suite. No adverse events were observed in the patients. Resected tissues from the patients were imaged and an average tumor-to-background signal ratio of about 5 to 1 with a sensitivity of about 80% and specificity of 100% was measured. Interestingly, in the first patient, there was a nodule that the pathologist identified as a lymph node upon visual examination. However, the nodule had activated the imaging agent and later was shown by histopathology to be a sarcoma.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A handheld medical imaging device comprising:
a body, wherein the body is constructed and arranged to be held in a user's hand; and
a rigid imaging tip, wherein a proximal portion of the rigid imaging tip is connected to and distally extends from the body, wherein a distal end of the rigid imaging tip defines a first plane with a field of view with a lateral dimension between 10 mm to 50 mm inclusively, wherein the rigid imaging tip includes a bend such that the rigid imaging tip includes a proximal portion and a distal portion, wherein the distal portion is angled by 25° to 65° inclusively relative to the proximal portion, wherein a length of the distal angled portion is between 10 mm to 65 mm, wherein an optical path passes through the rigid imaging tip from the distal end of the rigid imaging tip to a proximal end of the rigid imaging tip;
a photosensitive detector optically associated with the rigid imaging tip, wherein the photosensitive detector comprises a plurality of pixels; and
optics configured to focus the photosensitive detector on the first plane in at least one mode of operation, wherein there are no lenses located within the rigid imaging tip.

2. The handheld medical imaging device of claim 1, wherein the first plane at the distal end of the rigid imaging tip is at a fixed distance relative to the photosensitive detector, wherein the distal end of the rigid imaging tip includes a flat surface extending at least partially across the distal end of the rigid imaging tip, and wherein the photosensitive detector is focused on the first plane in at least one mode of operation.

3. The handheld medical imaging device of claim 1, wherein the distal end of the rigid imaging tip is open, and wherein the rigid imaging tip includes at least one opening on a side of the rigid imaging tip to provide surgical access to the distal end of the rigid imaging tip.

4. The handheld medical imaging device of claim 1, wherein the rigid imaging tip includes at least one orienting feature extending into the field of view.

5. The handheld medical imaging device of claim 1, further comprising a focusing element adapted to change a focus of the photosensitive detector from the first plane at a fixed distance relative to the photosensitive detector to a second plane located beyond the distal end of the rigid imaging tip.

6. The handheld medical imaging device of claim 1, wherein the optics are located between the photosensitive detector and the rigid imaging tip, wherein a magnification of the optics provide a field of view between 5µm to 100 µm for each pixel of the plurality of pixels.

7. The handheld medical imaging device of claim 1, wherein the lateral dimension of the field of view of the distal end of the rigid imaging tip is a diameter.

8. The handheld medical imaging device of claim 1, wherein the distal end of the rigid imaging tip includes a flat window transparent to preselected wavelengths.

9. The handheld medical imaging device of claim 1, further comprising a mirror or prism located within the rigid imaging tip that optically connects the proximal end to the distal end of the rigid imaging tip by bending the optical path around the bend in the rigid imaging tip.

10. The handheld medical imaging device of claim 1,
  wherein the rigid imaging tip includes a first portion and a second portion including the distal end, wherein the distal end includes an opening to provide access to a surgical bed, and wherein one or more supports extend between the first portion and the second portion.

11. The handheld medical imaging device of claim 10, wherein the one or more supports define at least one opening disposed on a side of the rigid imaging tip.

12. The handheld medical imaging device of claim 1, wherein a sidewall of the rigid imaging tip is opaque to preselected wavelengths.

13. The handheld medical imaging device of claim 1, wherein the lateral dimension of the field of view at the first plane at the distal end of the rigid imaging tip is greater than or equal to 25 mm.

14. The handheld medical imaging device of claim 1, wherein the rigid imaging tip is selectively removable from the body.

15. The handheld medical imaging device of claim 2, wherein the photosensitive detector has a depth of field, and wherein the flat surface at the distal end of the rigid imaging tip deflects by less than the depth of field when a five pound force is applied to the flat surface.

16. The handheld medical imaging device of claim 1, further comprising one or more illumination sources, wherein the optical path passes from the distal end of the rigid imaging tip to the photosensitive detector, wherein light passing through the first plane towards the photosensitive detector and light emitted from the one or more illumination sources both travel along the optical path through the rigid imaging tip.

17. The handheld medical imaging device of claim 1, further comprising a light directing element positioned between the photosensitive detector and the rigid imaging tip, wherein the light directing element is adapted to reflect light below a threshold wavelength towards the distal end of the rigid imaging tip and transmit light above the threshold wavelength towards the photosensitive detector.

18. The handheld medical imaging device of claim 17, wherein the threshold wavelength is less than an emission wavelength of a preselected imaging agent and greater than an excitation wavelength of the preselected imaging agent.

19. The handheld medical imaging device of claim 18, wherein the excitation wavelength and emission wavelength are both between 590 nm and 850 nm inclusively.

20. The handheld medical imaging device of claim 18, wherein the excitation wavelength and emission wavelength are both between 300 nm and 1,000 nm inclusively.

21. The handheld medical imaging device of claim 17, wherein the threshold wavelength is greater than a first excitation wavelength of a first illumination source associated with the light directing element.

22. The handheld medical imaging device of claim 1, wherein the optics magnify the field of view.

23. The handheld medical imaging device of claim 1, wherein the optics demagnify the field of view.

24. The handheld medical imaging device of claim 1, wherein the optics include an aperture with a diameter between 5 mm to 15 mm inclusively.

25. The handheld medical imaging device of claim 1, wherein the optics include an objective lens and an imaging lens.

26. The handheld medical imaging device of claim 1, wherein a depth of field of the optics is between 0.1 mm to 10 mm inclusively.

27. The handheld medical imaging device of claim 1, wherein a focal length from a distal-most lens of the optics to the distal end of the rigid imaging tip is between 10 mm and 40 mm inclusively.

28. A handheld medical imaging device comprising:
  a body, wherein the body is constructed and arranged to be held in a user's hand;
  a rigid imaging tip, wherein a proximal portion of the rigid imaging tip is connected to and distally extends from the body, wherein a distal end of the rigid imaging tip defines a first plane with a field of view with a lateral dimension between 10 mm to 50 mm inclusively, wherein the rigid imaging tip includes a bend such that the rigid imaging tip includes a proximal portion and a distal portion, wherein the distal portion is angled by 25° to 65° inclusively relative to the proximal portion, wherein a length of the distal angled portion is between 10 mm to 65 mm, and wherein an optical path passes through the rigid imaging tip from the distal end of the rigid imaging tip to a proximal end of the rigid imaging tip;
  a photosensitive detector optically associated with the rigid imaging tip, wherein the photosensitive detector comprises a plurality of pixels; and
  optics configured to focus the photosensitive detector on the first plane in at least one mode of operation, wherein a distal-most lens of the optics is located in the body.

* * * * *